United States Patent
Bramlet

[19]

[11] Patent Number: 5,976,139
[45] Date of Patent: Nov. 2, 1999

[54] SURGICAL FASTENER ASSEMBLY

[76] Inventor: Dale G. Bramlet, 2044 Brightwaters Blvd. NE., St. Petersburg, Fla. 33704

[21] Appl. No.: 08/680,620

[22] Filed: Jul. 17, 1996

[51] Int. Cl.⁶ .................................................. A61B 17/76
[52] U.S. Cl. .................................. 606/66; 606/65; 606/69
[58] Field of Search .................................. 606/66, 65, 68, 606/67, 63, 64, 62, 60, 61, 72, 73, 69, 70, 71

[56] References Cited

U.S. PATENT DOCUMENTS

| | | |
|---|---|---|
| 3,791,380 | 2/1974 | Dawidowski . |
| 4,632,101 | 12/1986 | Freedland .................................. 606/68 |
| 4,898,156 | 2/1990 | Gatturna et al. . |
| 4,946,468 | 8/1990 | Li . |
| 4,968,315 | 11/1990 | Gatturna . |
| 5,002,550 | 3/1991 | Li . |
| 5,007,910 | 4/1991 | Anapliotis et al. ........................ 606/65 |
| 5,041,116 | 8/1991 | Wilson ...................................... 606/65 |
| 5,046,513 | 9/1991 | Gatturna et al. . |
| 5,057,103 | 10/1991 | Davis ........................................ 606/63 |
| 5,192,303 | 3/1993 | Gatturna et al. . |
| 5,207,679 | 5/1993 | Li . |
| 5,217,486 | 6/1993 | Rice et al. . |
| 5,324,292 | 6/1994 | Meyers ...................................... 606/73 |
| 5,356,413 | 10/1994 | Martins et al. . |
| 5,534,004 | 7/1996 | Santangelo . |
| 5,578,035 | 11/1996 | Lin ............................................ 606/68 |
| 5,591,168 | 1/1997 | Judet et al. ............................... 606/65 |

*Primary Examiner*—Guy V. Tucker
*Attorney, Agent, or Firm*—Kenyon & Kenyon

[57] ABSTRACT

A surgical fastener assembly for coupling first and second bone portions across a fracture therebetween including an elongated anchor or bone screw insertable within the first bone such that one end portion of the anchor is disposed on one side of the fracture while a second end portion of the anchor is disposed on an opposite side of the fracture. A guide having a sleeve-like projection is fixedly secured to the second bone. The sleeve-like projection on the guide moves slidably along and is guided by the second end portion of the anchor. A compression screw assembly serves to operably secure the guide to the anchor such that the bone portions secured to each are maintained in compressive relationship relative to each other. A screw assembly for maintaining the guide in fixed relation relative to the bone portion to which it is secured is also disclosed.

53 Claims, 27 Drawing Sheets

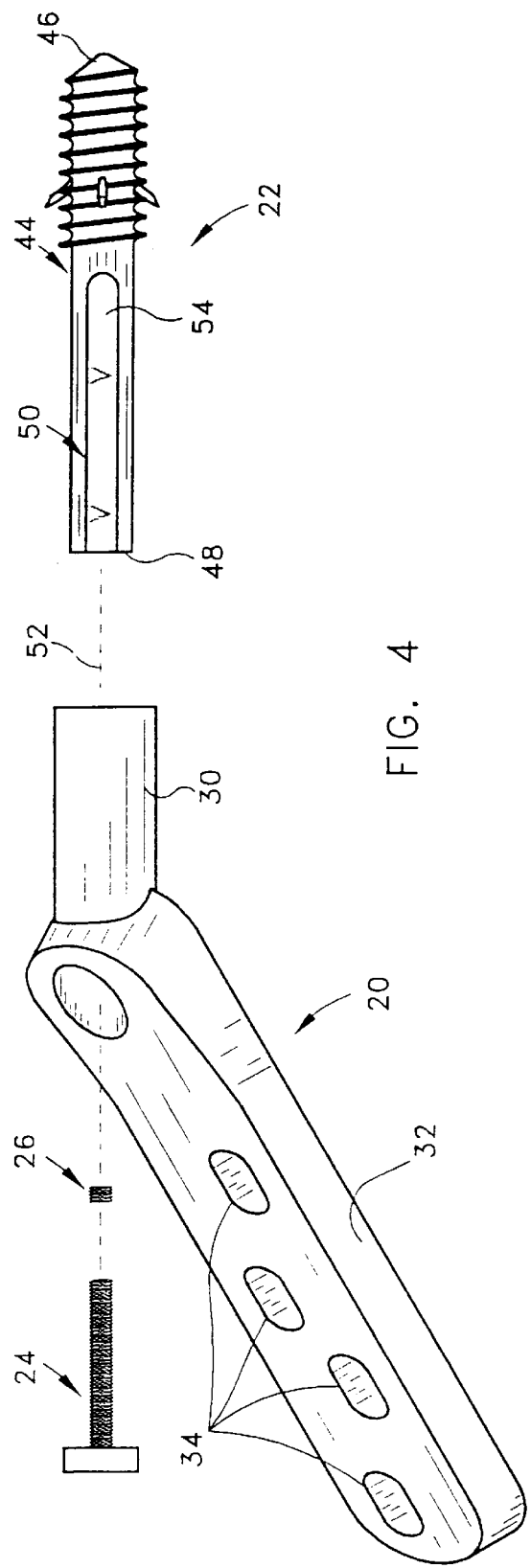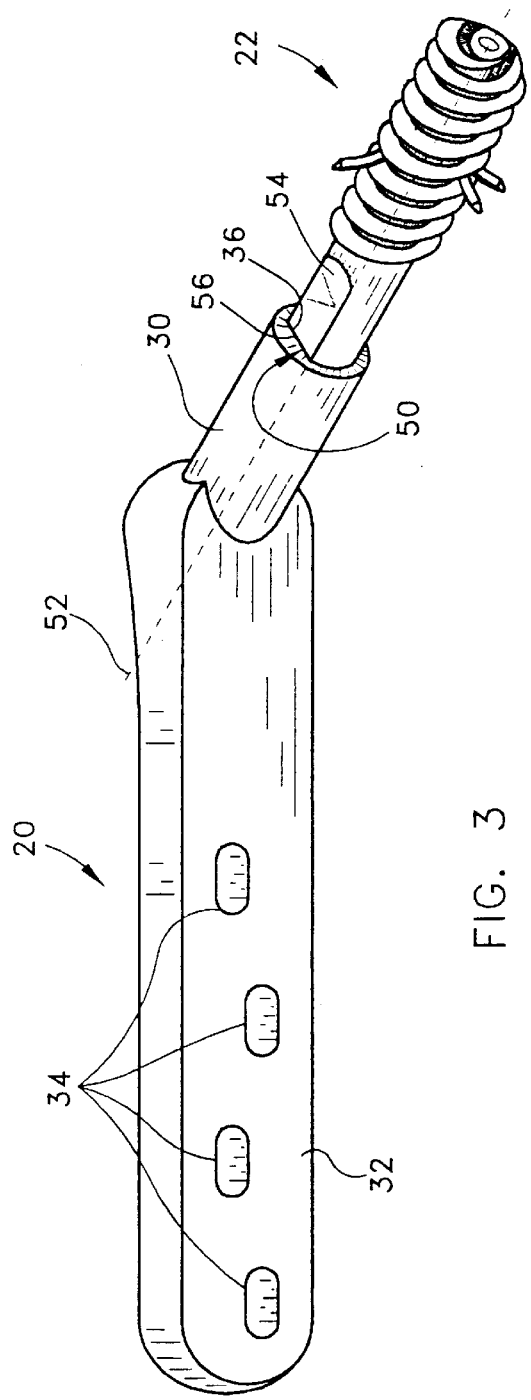
FIG. 4
FIG. 3

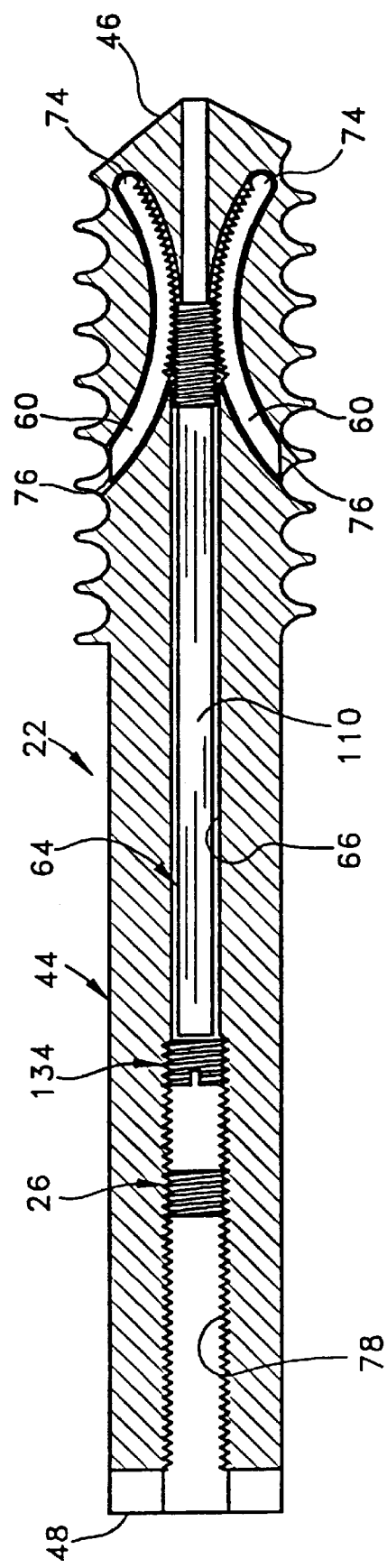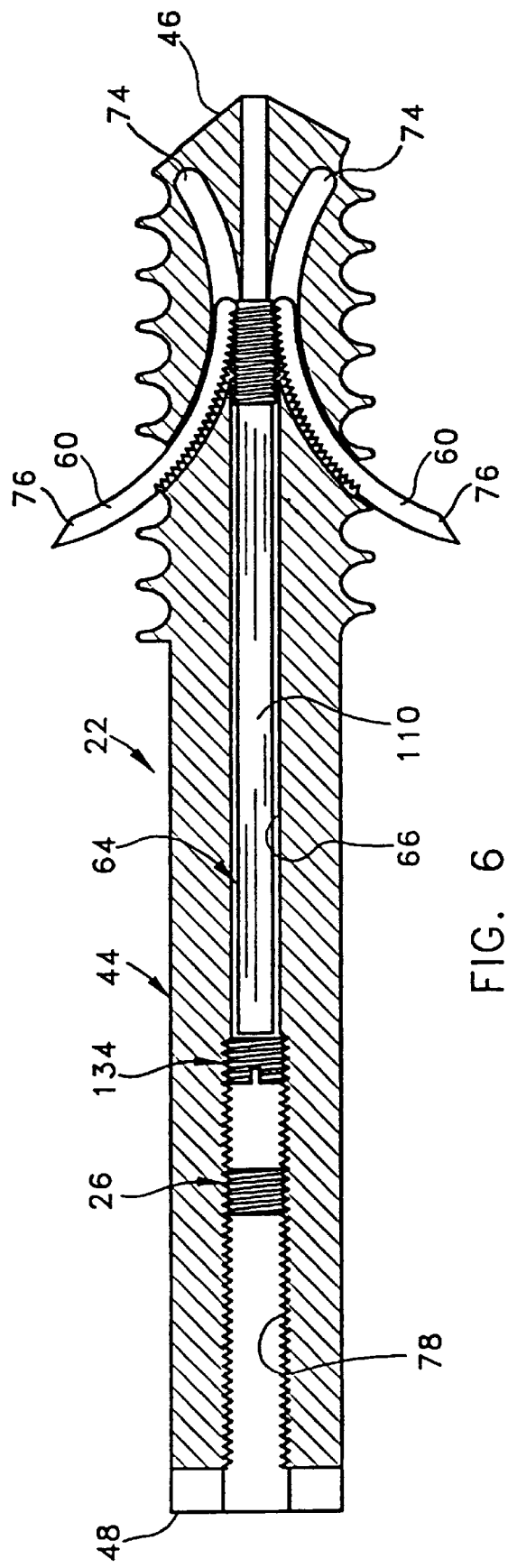

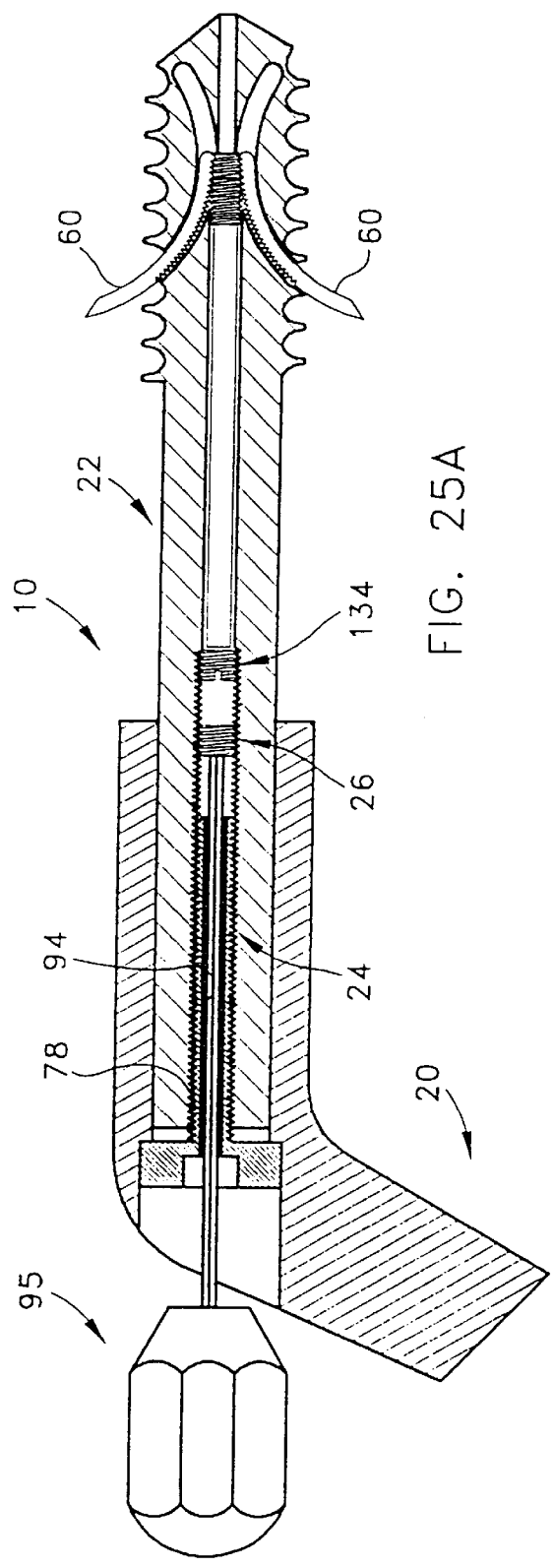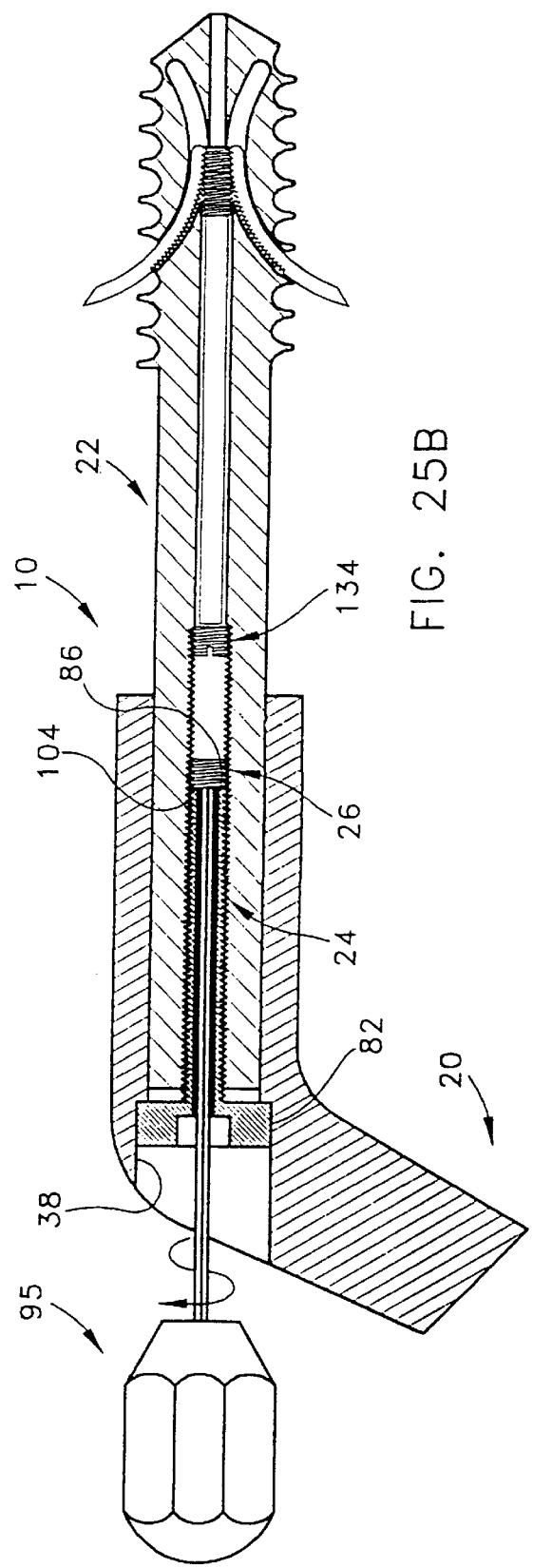

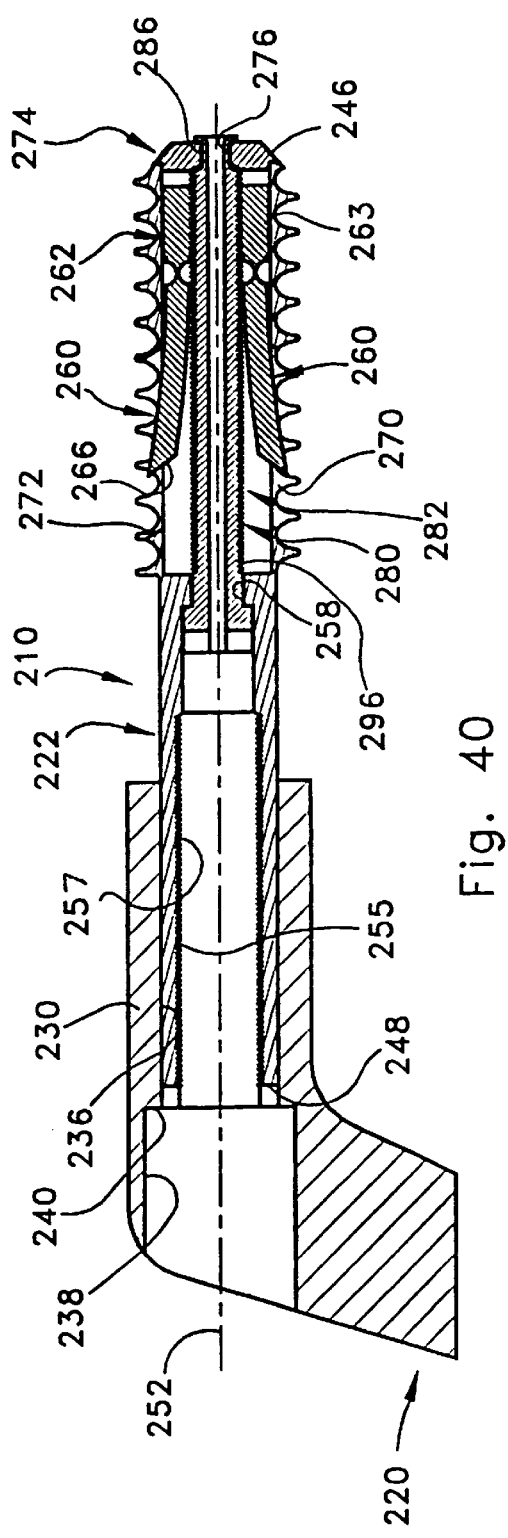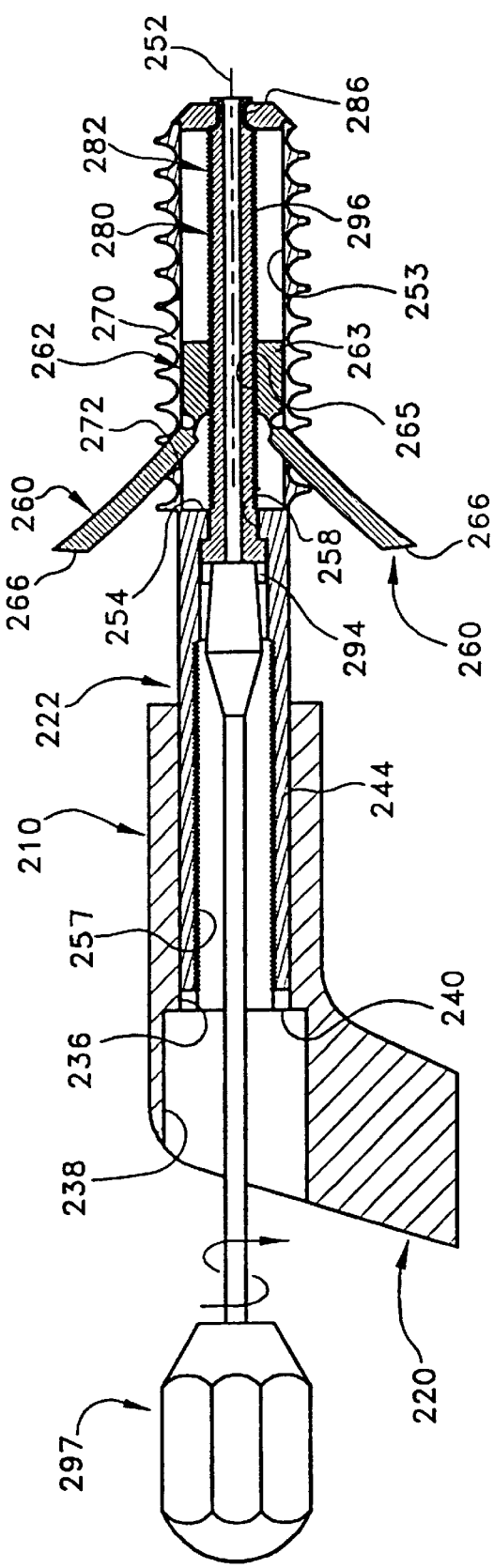
Fig. 40
Fig. 42

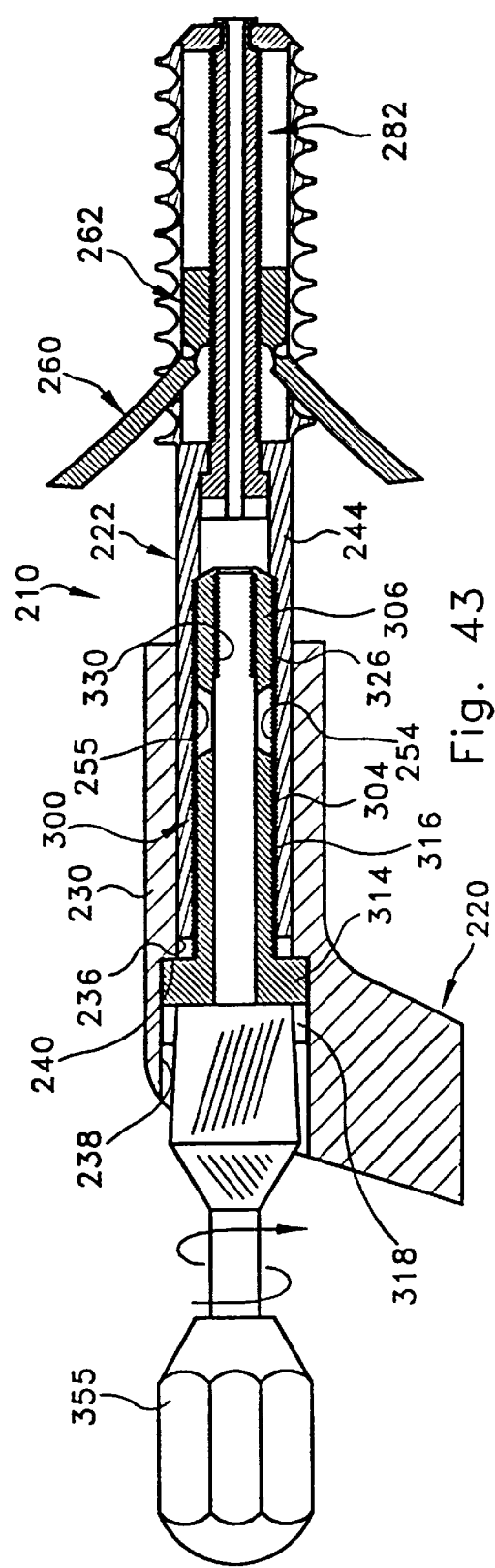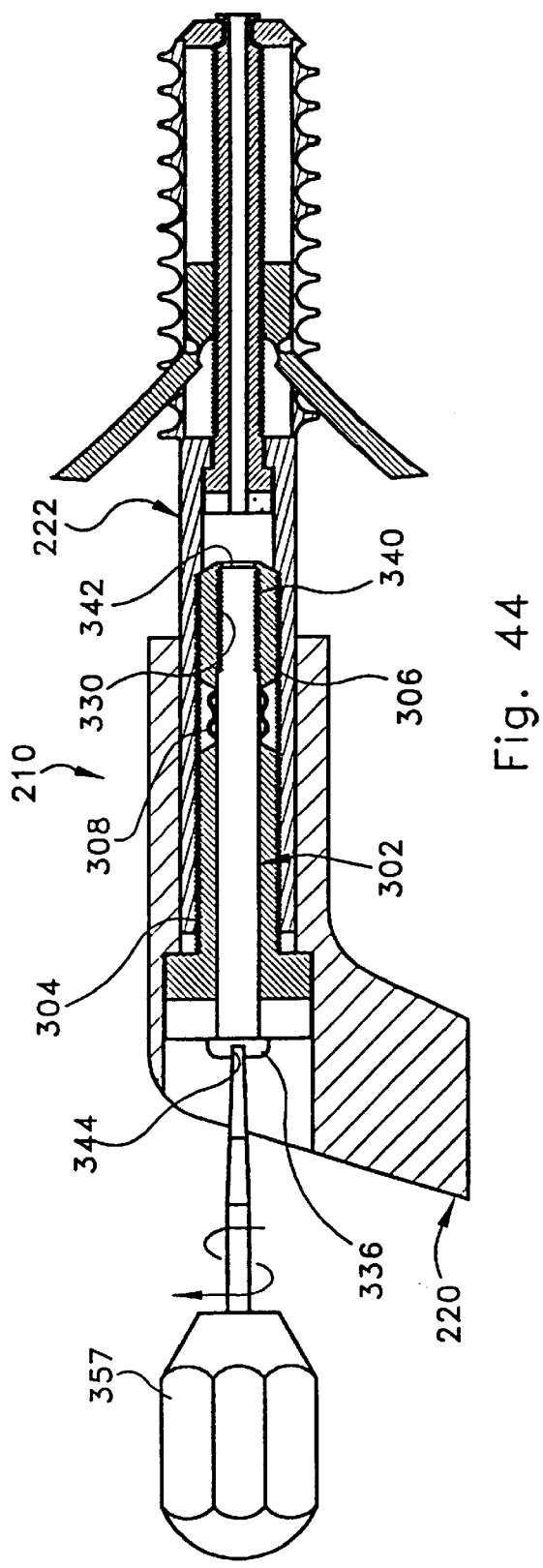

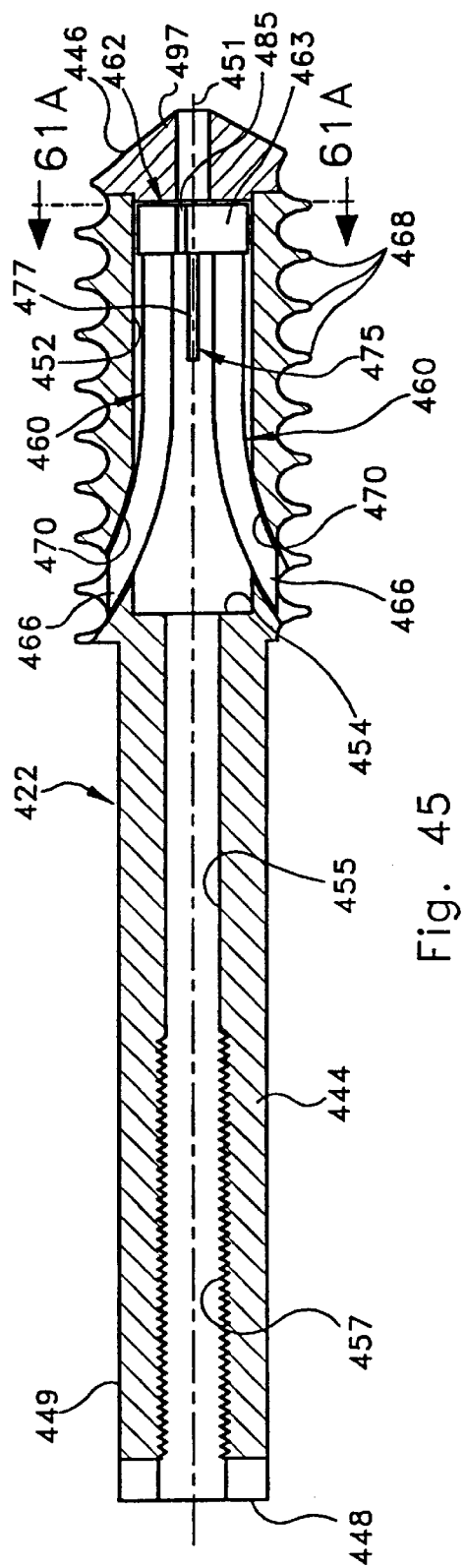
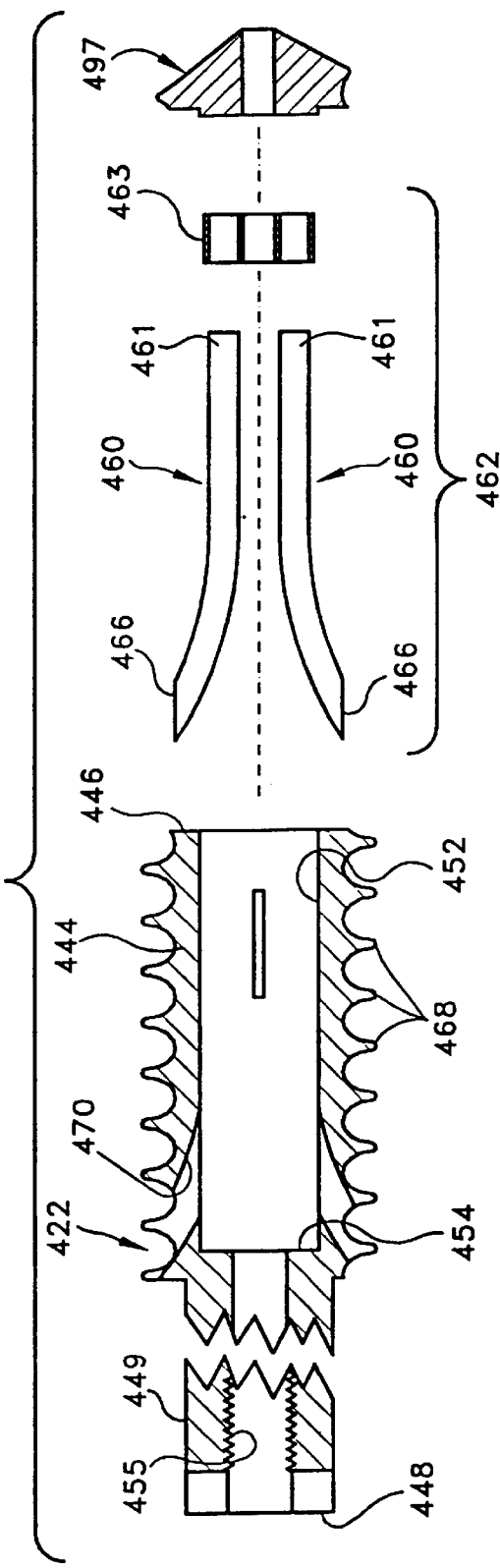
Fig. 45
Fig. 46

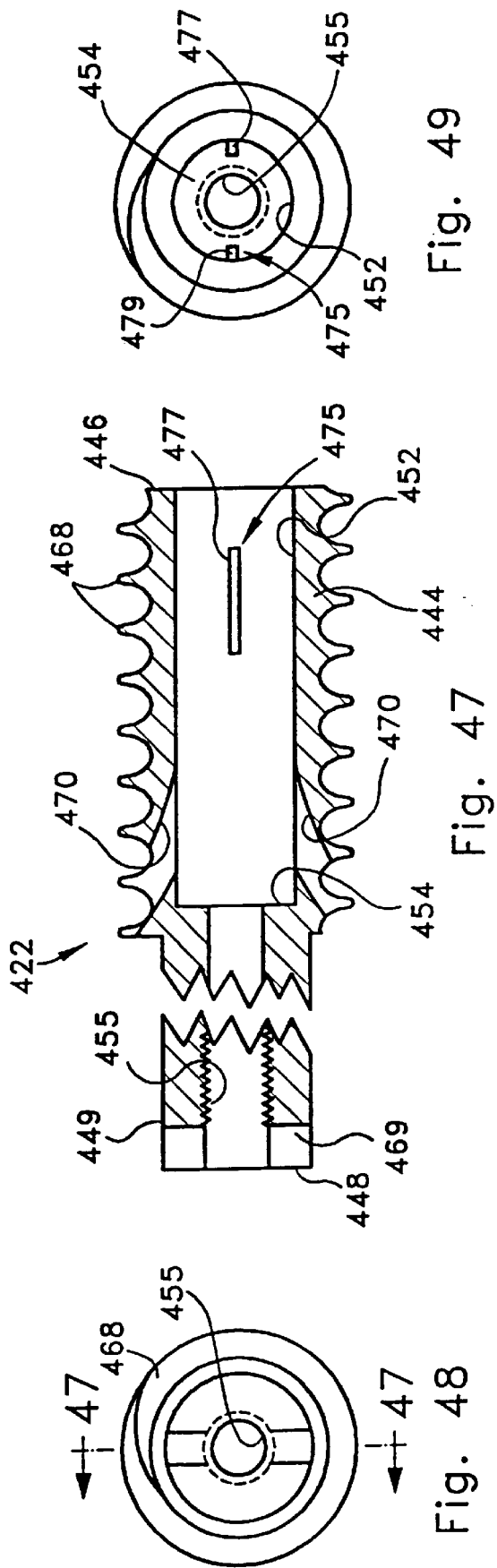
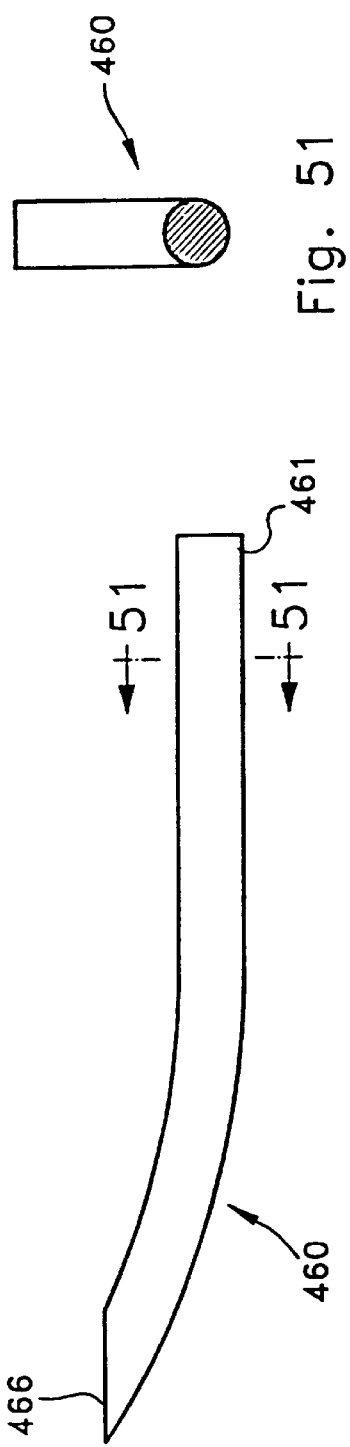

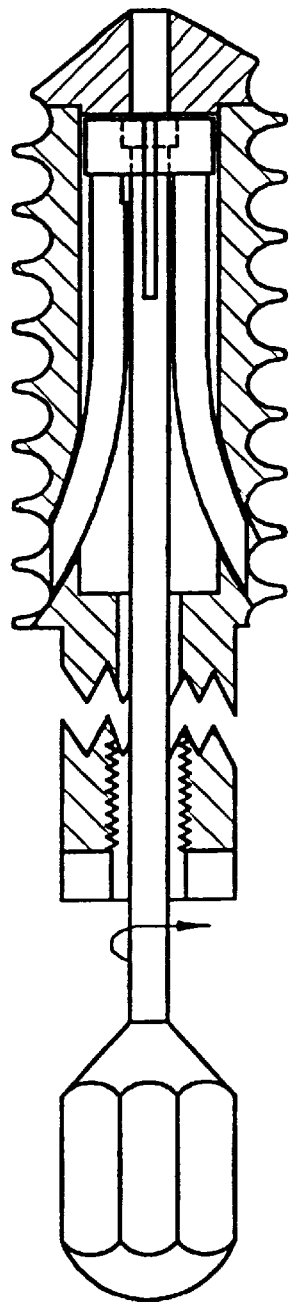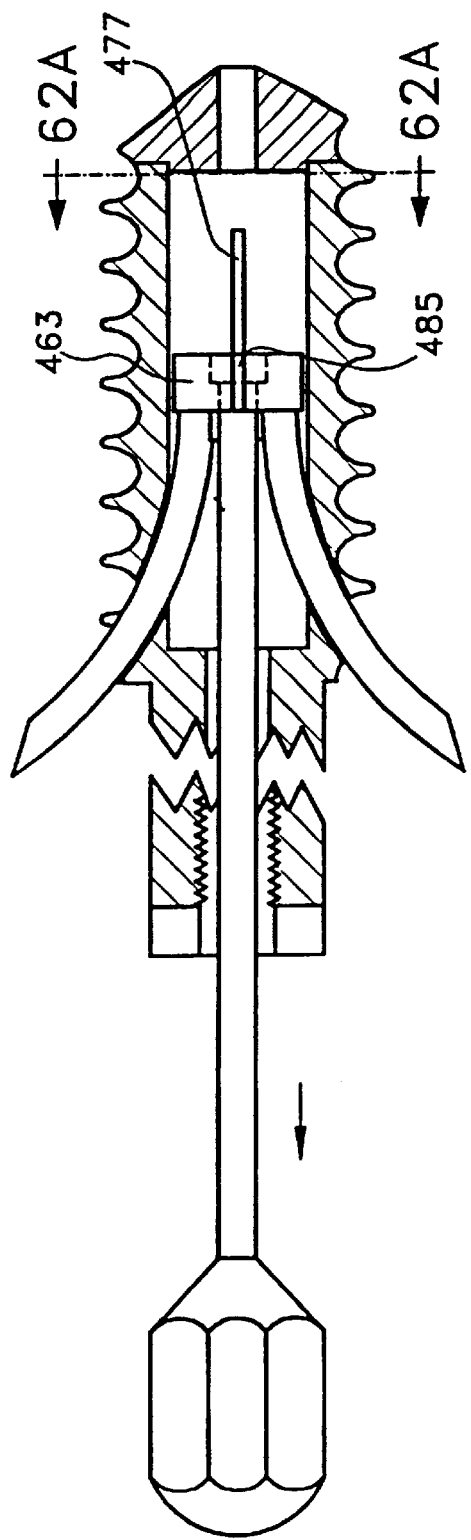
Fig. 61
Fig. 62

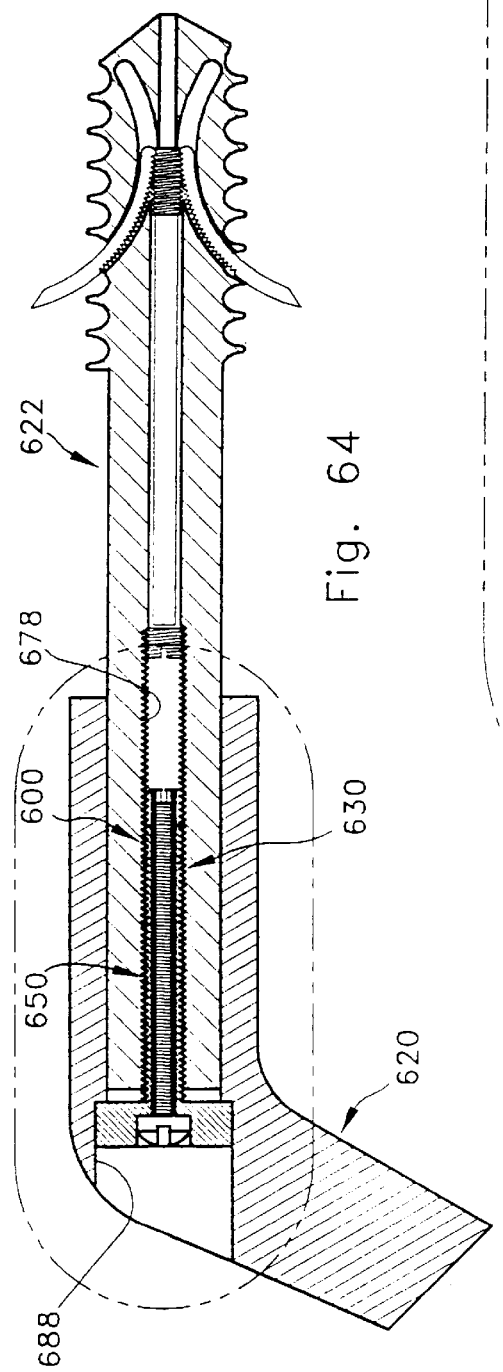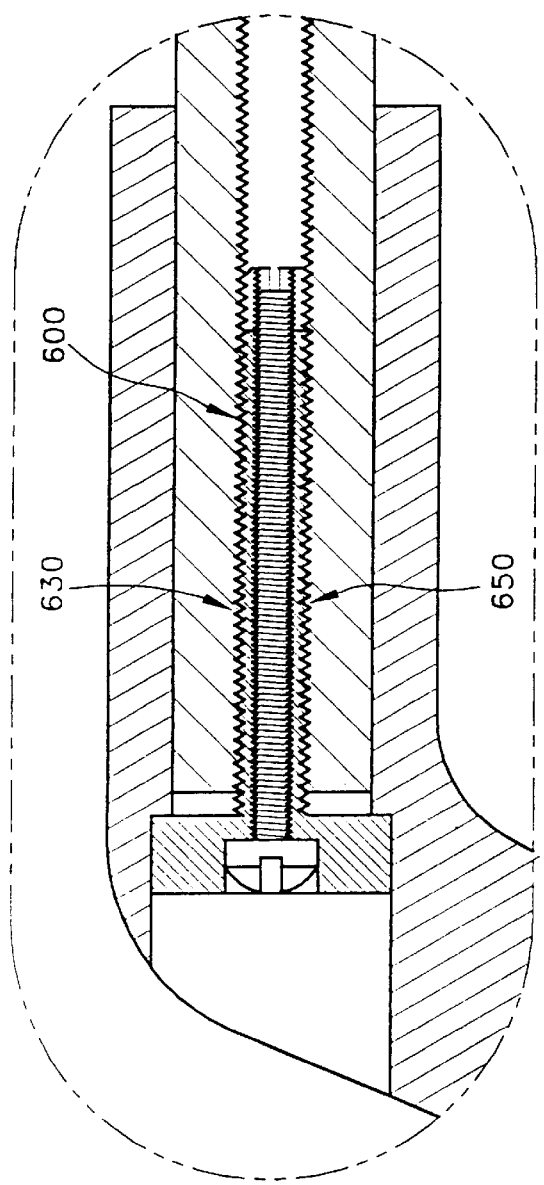

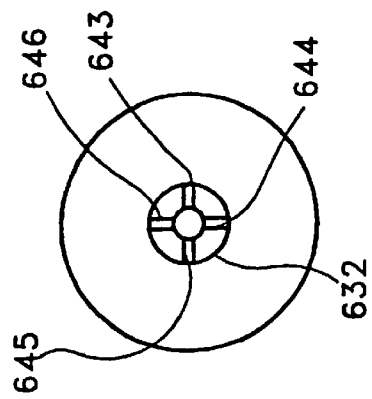
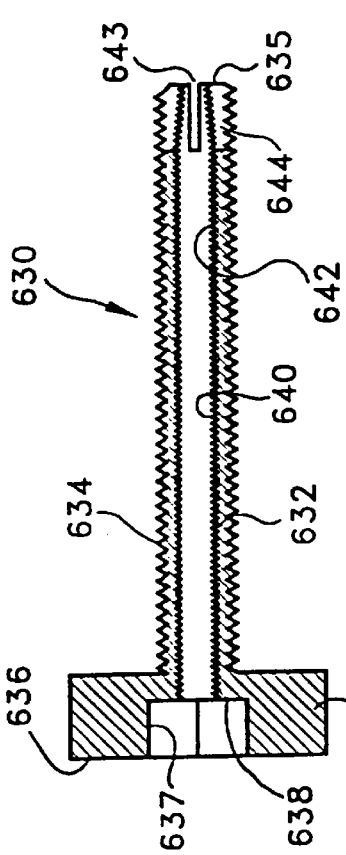
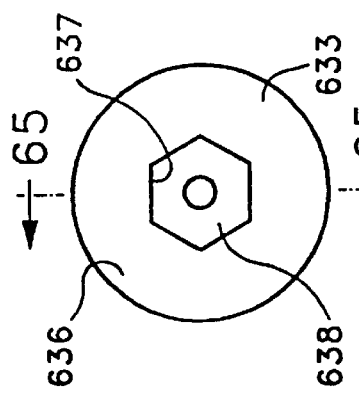
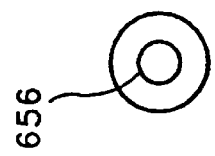
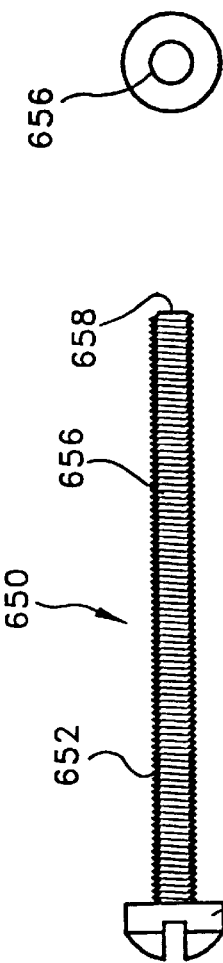
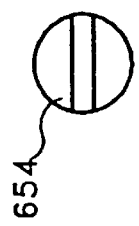

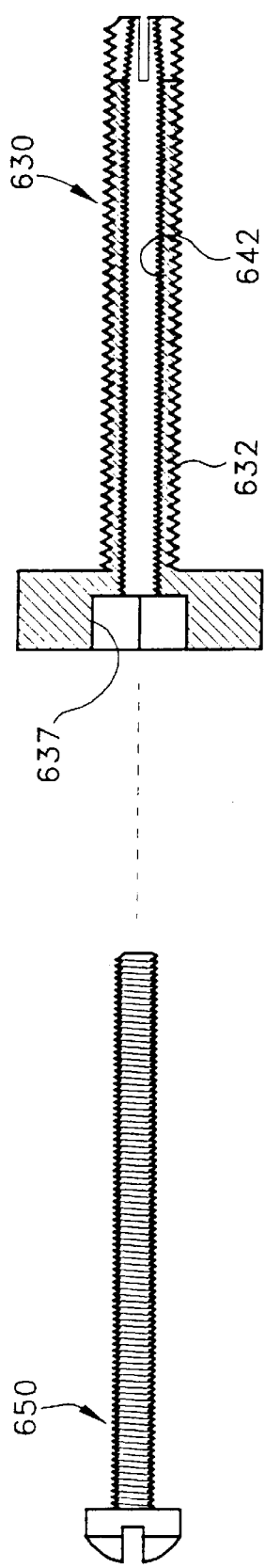
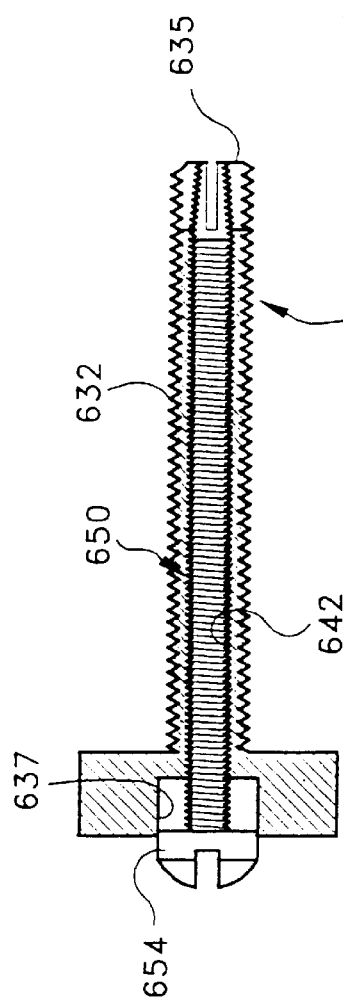
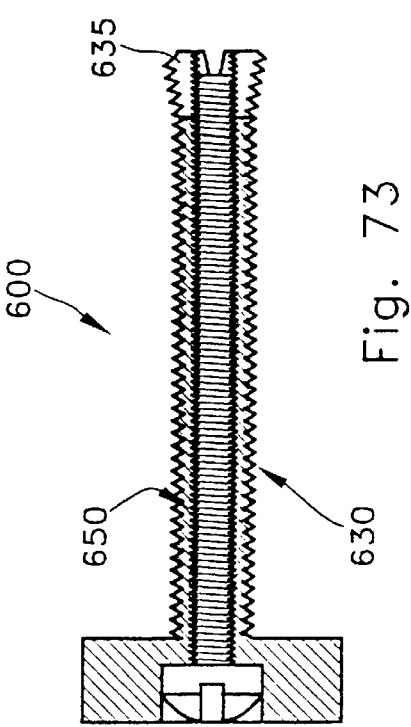
Fig. 71
Fig. 72
Fig. 73

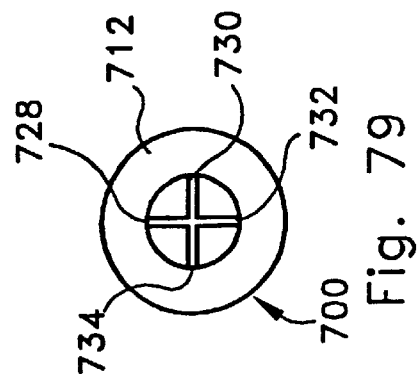
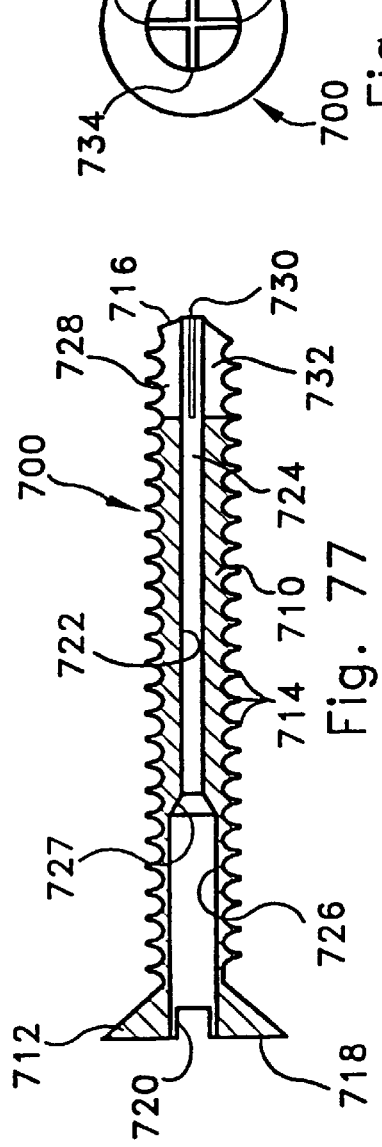
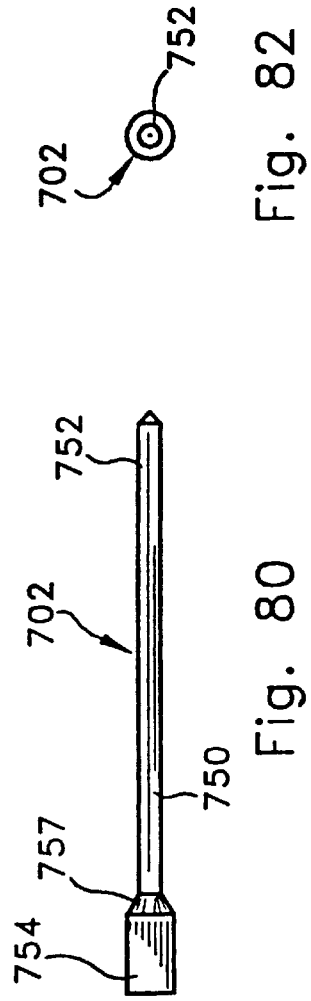
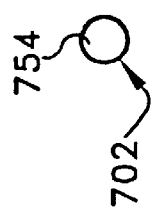
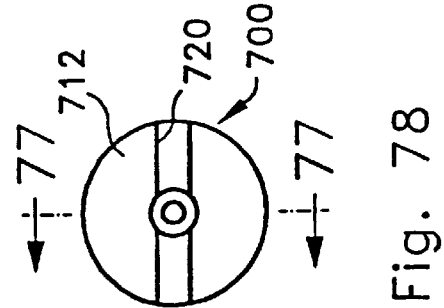

SURGICAL FASTENER ASSEMBLY

FIELD OF INVENTION

The present invention generally relates to a surgical fastener assembly for coupling first and second bone portions across a fracture therebetween and, more specifically, to a hip-pinning system for rigidly interconnecting a femoral head to the remaining portion of the femur and across a fracture in the area of the femur neck.

BACKGROUND OF THE INVENTION

A hip joint is a heavily stressed, load-carrying bone joint in the human body. It is essentially a ball and socket joint formed by the top of the femur which pivots within a cup-shaped acetabulum at the base of the pelvis. When a break or fracture occurs adjacent to the top of the femur, the separated portions of the femur must be held together while healing occurs.

There have been a number of techniques used historically for treatment of fractures of the proximal and distal ends of the femur. In early parts of this century, patients were merely placed in bed or in traction for prolonged periods, frequently resulting in deformity or death. In the 1930s, the Smith-Peterson nail was introduced, resulting in immediate fixation of hip fractures, early mobilization of the patient, and a lowered morbidity and mortality. A number of nails have been introduced for a fracture fixation about the femur in its proximal end, including the Jewett nail and, in more recent years, dynamic compression devices that allow capture of the most proximal fragments of the femur, compression of intertrochanteric and subtrochanteric fracture fragments, rigid fixation of the most proximal and distal fragments, and a sliding lag screw or anchor which fits within a barrelled side plate for allowing further compression of fragments as the patient ambulates and begins to bear weight on the fractured limb. The side plate is typically secured to the bone fragment with a series of screws or fasteners.

The use of a rigid, blade plate, has been used both at the proximal end of the femur for fixation of subtrochanteric femur fractures, and at the distal end for fixation of supracondylar and intercondylar fractures about the knee. Because these fractures can be technically challenging to fix, a dynamic compression screw, similar in many respects to a dynamic hip compression screw, but with a side plate design and angle similar to a blade plate, have been utilized for several years.

All of the known prior art, whether in the patient literature as disclosed above, or in commercial devices, fails to take into account the shifting of the lag screw or anchor and its compression screw in the barrel as the break heals and the fragments move closer together. When this movement occurs, the compression screw can back out of the lag screw and move away from the break and into the soft tissue causing discomfort, pain and a painful bursa. With osteopenic patients, the dynamic hip compression screws can loosen or erode through the superior bone of the head of the femur, resulting in joint penetration and destruction of the joint, producing arthritis. This can necessitate additional surgery for the removal of the hip compression screw, and replacement of the hip of the femur with a prosthesis. Similarly, the use of a dynamic compression screw in osteopenic patients may result in inadequate purchase of the lag screw threads within the bone, with resultant loss of fixation as the compression screw is used to compress the lag screw and resultant proximally fixed bone to the side plate and distally fixed bone. With loss of purchase of the lag screw or anchor within the head of the femur, compression forces are dissipated, and the implant device can fail, resulting in a nonunion or malunion of the fracture fragments. Similar loss of fixation can occur about the supracondylar and intercondylar fractures of the distal femur with osteopenic patients.

To prevent loss of fixation with compression and to decrease required removal of the anchoring lag screw within the femoral head in osteopenic patients, some devices have been modified to increase purchase of the anchoring lag screw within the femoral head, by enlarging the lag screw, or by alternative means of fixation of the proximal fragment with a molley bolt concept. This later device has not gained as wide acceptance with surgeons in the United States as it differs from traditional lag screw techniques of screwing in the device, giving the surgeon a sense of "feel" of the degree of purchase of the lag screw with the bone, and, thus, an idea of the degree to which the surgeon may compress the lag screw and side plate assembly without loss of fixation by "over-compression."

As the lag screw slides within the barrel of the side plate, it can become prominent on the side of patients who are cachectic. Frequently, the compression screw will back out once implanted, leading to further prominence of the device and possible erosion through the skin. This can lead to premature or unwanted additional surgery for removal of the compression screw or device increasing the morbidity, rate of infection and mortality caused by additional surgery, frequently in frail elderly patients who least are able to withstand additional surgical insult to their body. Many surgeons remove the compression screw for this very reason, to prevent it from backing out. With removal of the compression screw, however, the possibility of disassembly of the device can occur with resultant failure of fracture fixation and the necessity for further surgical operations. Some hip pinning systems have been modified to prevent the inadvertent disassembly of the lag screw and side plate by constraining the degree to which the lag screw and side plate can dissociate and by increased modularity of the side plate and lag screw component, enabling perhaps a smaller incision on the patient. This modularity, however, introduces another theoretical variable of potential loss of fixation of the side plate in the lag screw portions of the devices. Furthermore, the side plates can loosen their purchase from the distal fragments by biological resorption with resultant loss of purchase of fixation of the screws holding the side plate to the lateral side of the femur. This can happen in either the dynamic hip compression screws or the dynamic compression screws used about distal condylar fractures of the femur or for subtrochanteric fractures of the femur. Closer placement of the screw holes in side plate, enabling more threads per unit of length of the femur, or alternating the number and location of holes in the side plate with a broader side plate have been advocated to reduce the incidence of loss of purchase of the side plate. The use of a distal compression screw allows more proximal compression in the longitudinal axis of the femur, to increase compression at the fracture site.

Furthermore, the screws or fasteners used to hold the side plate to the lateral femur often become loose as bone is resorbed about the external threading on the screws. Thus, the side plate often becomes loose from the bone, resulting in failure of the implant and loss of fixation of the fracture.

Thus, there is a need and a desire for an improved hip pinning or surgical fastener assembly that allows greater purchase of the lag screw within the femoral head of the hip bone while yielding a "feel" of fixation to the surgeon during insertion of the lag screw. Such a pinning system for fixation assembly should furthermore be designed to allow a compression screw to remain permanently in place after surgery thus maintaining the degree of compression between the lag screw and side plate. It is also desirable to prevent the screws used to maintain the side plate in fixed relation relative to the bone fragment from loosening thereby maintaining the side plate in secure relation relative to the bone to which it was initially secured.

SUMMARY OF THE INVENTION

In view of the above, and in accordance with the present invention, there is provided an improved surgical fastener assembly for coupling first and second bone portions across a fracture therebetween. The surgical fastener assembly comprises an elongated anchor or bone screw insertable within the first bone such that one end portion of the anchor is disposed on one side of the fracture while a second end portion of the anchor is disposed on an opposite side of the fracture. A guide having a sleeve-like projection is fixedly secured to the second bone. The sleeve-like projection on the guide moves slidably along and is guided by the second end portion of the anchor. A compression screw assembly serves to operably secure the guide to the anchor. According to one form of the invention, the compression screw assembly includes a cannulated compression screw having an enlarged head portion and an externally threaded shank portion. The shank portion of the cannulated compression screw extends into threaded engagement with the anchor while the head portion of the cannulated screw operably engages with the guide such that rotation of the fastener draws the first and second bones into compressive relationship relative to each other. The cannulated compression screw defines an axial bore opening to opposite ends thereof. This form of the compression screw assembly further includes a retainer operably associated with the second end of and positionable relative to the compression screw for releasably locking the screw to the anchor thereby preventing axial displacement of the guide in a direction away from the anchor.

Preferably, both the anchor and the guide are formed from a material that is biocompatible with the bone tissue. In a most preferred form of the invention, the anchor is formed from a material chosen from the class comprised of: titanium, a titanium alloy, stainless steel, or cobalt chromium alloy. Similarly, the guide is preferably formed from a material chosen from the class comprised of: titanium, a titanium alloy, stainless steel, or cobalt chromium alloy.

To enhance the purchase of the surgical fastener assembly within the bone, the anchor is preferably provided with external threading extending over and along an axial length thereof for fastening the anchor within the first bone. Preferably, the second end of the anchor is configured to releasably accommodate a driving tool capable of imparting turning movements to the anchor such that the external threading on the anchor engages the bone substance of the first bone.

The cannulated configuration of the compression screw allows a tool to be inserted therethrough. In this form of the invention, the retainer is treadably associated with the second end of the anchor. The retainer is preferably configured to operably and releasably engage with the tool extendable through the cannulated screw whereby turning movements can be imparted to the retainer. As such, after the proper compressive relationship or "feel" is developed by the surgeon between the guide and the anchor as through turning the compression screw, the surgeon then secures the compression screw in place by moving the retainer into locked relationship with the screw thereby preventing rotation of the screw relative to the anchor.

The guide preferably defines an open ended recess sized to accommodate the head portion of the compression screw therewithin. The recess is configured such that no portion of the compression screw axially extends beyond the guide after the guide is arranged in operable combination with the anchor thereby inhibiting injury to the patient.

The present invention is particularly useful as part of a hip pinning system for compressively interconnecting first and second fractured bone segments. The hip pinning system according to the present invention preferably includes an axially elongated bone screw defining an elongated axis and having external threading extending axially therealong for anchoring the leading end portion of the bone screw endwise within the first bone segment and such that the leading end portion of the bone screw is disposed to one side of the fracture. A trailing end portion of the bone screw is disposed on an opposite side of the fracture. The bone screw defines an elongated axial bore extending along the length thereof. A guide is adapted to be fixedly secured to the bone screw. A projection on the guide is guided by and along the second end portion of the bone screw. A compression screw assembly, including a compression screw having an enlarged head portion and an externally threaded shank portion, is further included as part of the hip pinning system. The shank portion of the compression screw extends into threaded engagement with the trailing end portion of the bone screw. The head portion of the compression operably engages with the guide such that rotation of the compression screw draws the first and second bone segments into compressive relationship relative to each other.

To promote purchase of the bone screw within the bone fragment, a series of fasteners or pins are arranged in combination with the bone screw. Each fastener is carried by the bone screw and is positively movable between retracted and extended positions. When in their retracted positions, the fasteners offer no operable anchoring affect to the bone screw within the bone tissue. When the fasteners or pins are in their extended position, however, they extend outwardly from the bone screw while remaining in operable combination therewith to secure the bone screw within the bone substance. The present invention furthermore includes a mechanism arranged in operable combination with and for positively moving the fasteners from their retracted position to their extended position. Preferably, the fasteners are movable endwise relative to the insert. Another salient feature of the present invention concerns the ability to operate the mechanism such that the fasteners can be positively retracted from their extended position to a retracted position in those circumstances where it becomes necessary.

The mechanism for moving the fasteners or pins positively in opposite directions can be of any suitable type that is manually operated to allow the surgeon control over displacement of the fasteners. In one form of the invention, the mechanism comprises a driver mounted for rotation within a cavity defined by the bone screw. The driver has external threading extending along an axial portion thereof for engaging with serrations on each of the fasteners whereby each fastener is endwise and positively displaced in either direction of travel depending upon the direction of rotation of the driver.

In another form of the invention, the mechanism for moving the fasteners outwardly relative to the bone screw thereby promoting securement of the bone screw within the bone substance comprises a driver that is axially and endwise movable relative to the bone screw. The driver is selectively engagable with the fasteners such that endwise displacement of the driver correspondingly effects positive endwise displacement of the fasteners relative to the bone screw.

According to another form of the invention, the compression screw assembly of the surgical anchor assembly comprises a multi-piece assembly including an elongated compression screw and driver. The compression screw preferably has a cannulated configuration. External threading extending axially along the compression screw serves to allow a shank portion of the compression screw to be engaged with the second end of the anchor while the head portion of the screw operably engages with the guide. At a distal end thereof, the compression screw is provided with expandable locking flanges. When the screw is arranged in operable combination with the anchor of the surgical fastener assembly, the driver is inserted into an operative relationship with the compression screw thereby forcibly expanding the flanges and thereby axially fixing the compression screw in predetermined relationship relative the second end of the bone screw or anchor.

According to another aspect of the present invention, a series of fasteners or screws are used to secure the guide of the surgical fastener assembly to one of the bones. As is conventional, the guide is provided with a series of apertures or openings that allow the fasteners or screws to pass endwise therethrough. In one form, each fastener or screw for securing the guide to the bone comprises a cannulated screw having a shank portion and a head portion. The shank portion is sized to extend endwise through the openings in the guide and through the bone to which the guide is to be attached. Accordingly, and as it may be appreciated, various size screws may be provided to allow the surgeon to custom fit the screw to the patient undergoing the operation. The shank portion of the screw is sized such that a distal end of the shank terminates approximate to that side of the bone opposite from the guide. Moreover, the shank portion has external threading extending axially toward the head portion from a distal end thereof to promote purchase of the screw assembly into the bone substance. The head portion of the screw is suitably configured to cooperate with and secure the guide about the elongated axis of the screw.

At the distal end of the screw, a lock is provided. The lock is configured to expand outwardly in response to the driver being inserted through the axial opening defined by the cannulated screw. Accordingly, the screw passes through the guide and is fastened in the bone such that the distal end of the screw proximates the surface of the bone opposite from the head portion of the screw. The lock is operably associated with and axially extends beyond the bone opposite from the head portion of the screw. In a preferred form, the lock is arranged at a distal end of the screw. Then, the driver is inserted through the screw and into the lock. The axial movement of the driver through the screw and into operable combination with the lock causes radial expansion of the lock thereby preventing the screw from inadvertently rotating and becoming disassociated from the guide.

Regardless of which embodiment is utilized, with the present invention, the surgeon is provided with the ability to compress the bone fragments into a predetermined compressive relationship with each other. The lag screw or anchor is insertable into the bone until the appropriate "feel" is provided to the surgeon. Thereafter, the lock associated with the combination with the cannulated compression screw is operated to maintain the compressive relationship between the guide and the bone screw. As such, and while maintaining a proper compressive relationship between the bone fragments, the lock or retainer prevents the compressive screw from inadvertently turning thereby preventing axial displacement of the guide in a direction away from the opposite end of the bone screw or anchor.

To enhance purchase of the anchor or bone screw within the bone, another salient feature of the present invention concerns the ability to provide a series of fasteners that are carried with the bone screw or anchor and are operable in response to a driving mechanism that positively displaces the fasteners in opposite end-wise directions. The ability to positively move the fasteners radially outwardly from the bone screw enhances the purchase of the bone screw within the bone substance.

Another object of the present invention is to enhance securement of the guide to a bone. In this regard, a screw is provided with a lock that is expandable in response to driver being inserted endwise through a cannulated screw. Expansion of the lock prevents inadvertent turning of the screw thereby maintaining the guide in fixed relationship relative to the bone.

These and other objects, aims and advantages of the present invention will become readily apparent from the following detailed description, the drawings, and the appended claims.

DESCRIPTION OF THE DRAWINGS

FIG. 3 is an assembled perspective view of the present invention;

FIG. 4 is a disassembled side elevational view illustrating component parts of one form of the present invention;

FIG. 5 is a longitudinal sectional view through a fastener forming part of the present invention;

FIG. 6 is a sectional view similar to FIG. 5 but showing pins or barbs of the fastener in an extended position;

FIG. 25A illustrates assembly of the surgical anchor assembly according to one form of the invention with the pins or barbs extended and a tool positioned to engage the retainer illustrated in FIGS. 21 through 25;

FIG. 25B is similar to FIG. 25A but illustrates further assembly of the surgical anchor assembly according to one form of the invention with the pins or barbs extended and a tool for moving the retainer illustrated in FIGS. 21 through 25 into operable engagement with the compressive cannulated fastener illustrated in FIGS. 16 through 20;

FIG. 40 is a view similar to FIG. 5 but showing a second embodiment of the present invention;

FIG. 42 is a view similar to FIG. 40 schematically illustrating distention of the pins or barbs relative to the anchor;

FIG. 43 is a view similar to FIG. 42 but showing an alternative form of compression screw assembly arranged in operable combination with the anchor and a conventional side plate;

FIG. 44 is a view similar to FIG. 43 but showing a driver of the compression screw assembly arranged in a locking relationship relative to a compression screw;

FIG. 45 is a longitudinal sectional view of a third embodiment of a surgical anchor assembly according to the present invention with an alternative form of pins operably associated therewith and in a retracted relationship therewith;

FIG. 46 is a fragmentary longitudinal sectional view showing component parts of the third embodiment of the present invention in exploded or disassembled relation relative to each other;

FIG. 47 is a fragmentary longitudinal sectional view of an anchor or insert forming part of the third embodiment of the present invention;

FIG. 48 is a left end view of the anchor illustrated in FIG. 47;

FIG. 49 is a right end view of the anchor illustrated in FIG. 47;

FIG. 50 is a side elevational view of a pin forming part of the third embodiment of the present invention;

FIG. 51 is a sectional view taken along line 51—51 of FIG. 50;

FIG. 61 is sectional view showing the tool illustrated in FIGS. 59 and 60 arranged in operable combination with a slide assembly forming part of the third embodiment of the present invention and with the pins or barbs shown in retracted position relative to the anchor;

FIG. 62 is a view similar to FIG. 61 but showing the tool in operable relationship with the slide of the slide assembly for forcibly extending the pins or barbs radially outwardly from the anchor;

FIG. 64 is an another form of surgical anchor assembly having an alternative form of a compression screw assembly for holding the anchor and guide in compressive relationship relative to each other;

FIG. 64A is an enlarged sectional view of the compression screw assembly encircled in FIG. 64;

FIG. 65 is a longitudinal sectional view of a compression screw forming a component part of the compression screw assembly illustrated in FIGS. 64 and 64A;

FIG. 66 is a left end elevational view of the compression screw illustrated in FIGS. 65;

FIG. 67 is a right end elevational view of the compression screw illustrated in FIGS. 65;

FIG. 68 is an elevational view of a driver used in combination with the compression screw assembly illustrated in FIGS. 65 through 67;

FIG. 69 is a left end elevational view of the driver illustrated in FIG. 68;

FIG. 70 is a right end elevational view of the driver illustrated in FIG. 68;

FIG. 71 is a schematic partially sectional elevational view of the compression screw (FIG. 65) and driver (FIG. 68) shown in exploded or disassembled relation relative to each other;

FIG. 72 is a schematic representation of the driver being illustrated in partial relation with the compression screw;

FIG. 73 is a schematic representation of the driver being illustrated in complete relation with the compression screw;

FIG. 77 is a longitudinal sectional view of a compression screw forming part of the screw assembly illustrated in FIGS. 75 and 76;

FIG. 78 is a left end view of the compression shown in FIG. 77;

FIG. 79 is a right end view of the compression screw illustrated in FIG. 77;

FIG. 80 is a side elevational view of a driver used in combination with the screw assembly illustrated in FIGS. 75 and 76;

FIG. 81 is a left end elevational view of the driver illustrated in FIG. 80;

FIG. 82 is a right end elevational view of the driver illustrated in FIG. 80.

DETAILED DESCRIPTION OF THE PRESENT INVENTION

Figure 1:
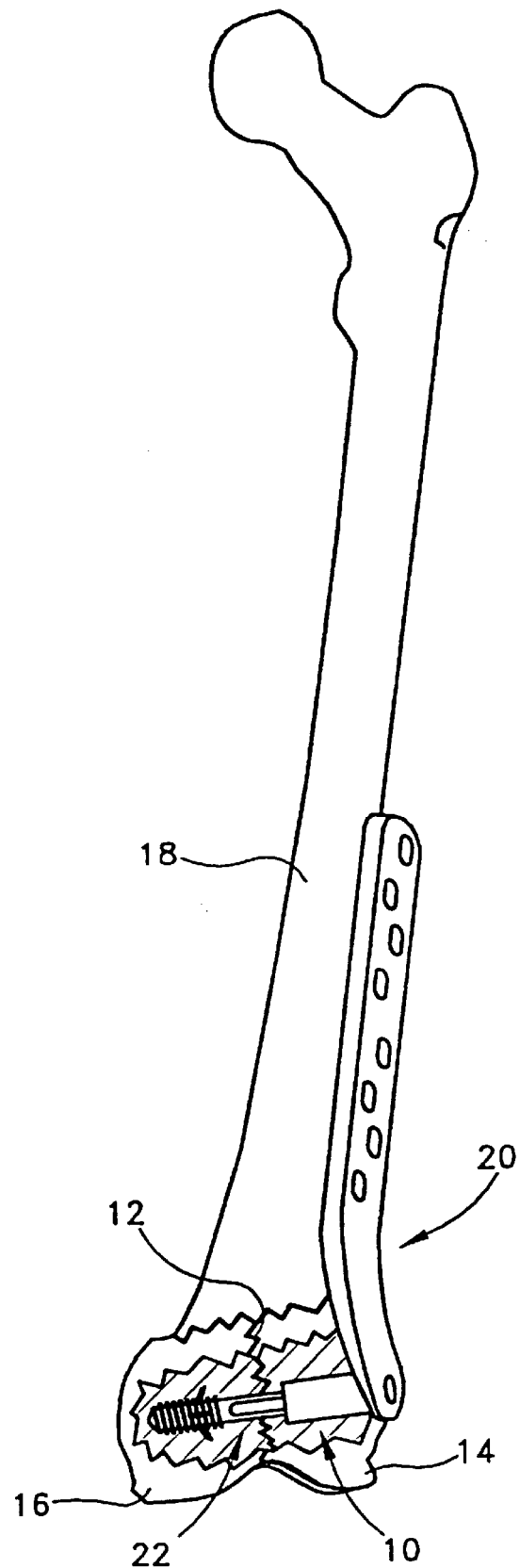
FIG. 1 is a view showing a surgical fastener assembly according to the present invention in operable association with and extending across a condylar fracture.

While the present invention is susceptible of embodiment in various forms, there is shown in the drawings and will hereinafter be described preferred embodiments of the invention with the understanding that the present disclosure is to be considered as setting forth exemplifications of the invention which are not intended to limit the invention to the specific embodiments illustrated.

Referring now to the drawings, wherein like reference numerals refer to like parts throughout the several views, there is schematically represented in FIG. 1 one form of a fastener assembly 10 used to compressively secure fractured first and second bone fragments across the fracture therebetween. In the illustrated embodiment, the surgical fastener assembly 10 is used to set a condylar fracture accurately along a fracture line 12 disposed between proximal and distal portions 14 and 16, respectively, of a bone 18.

Figure 2:
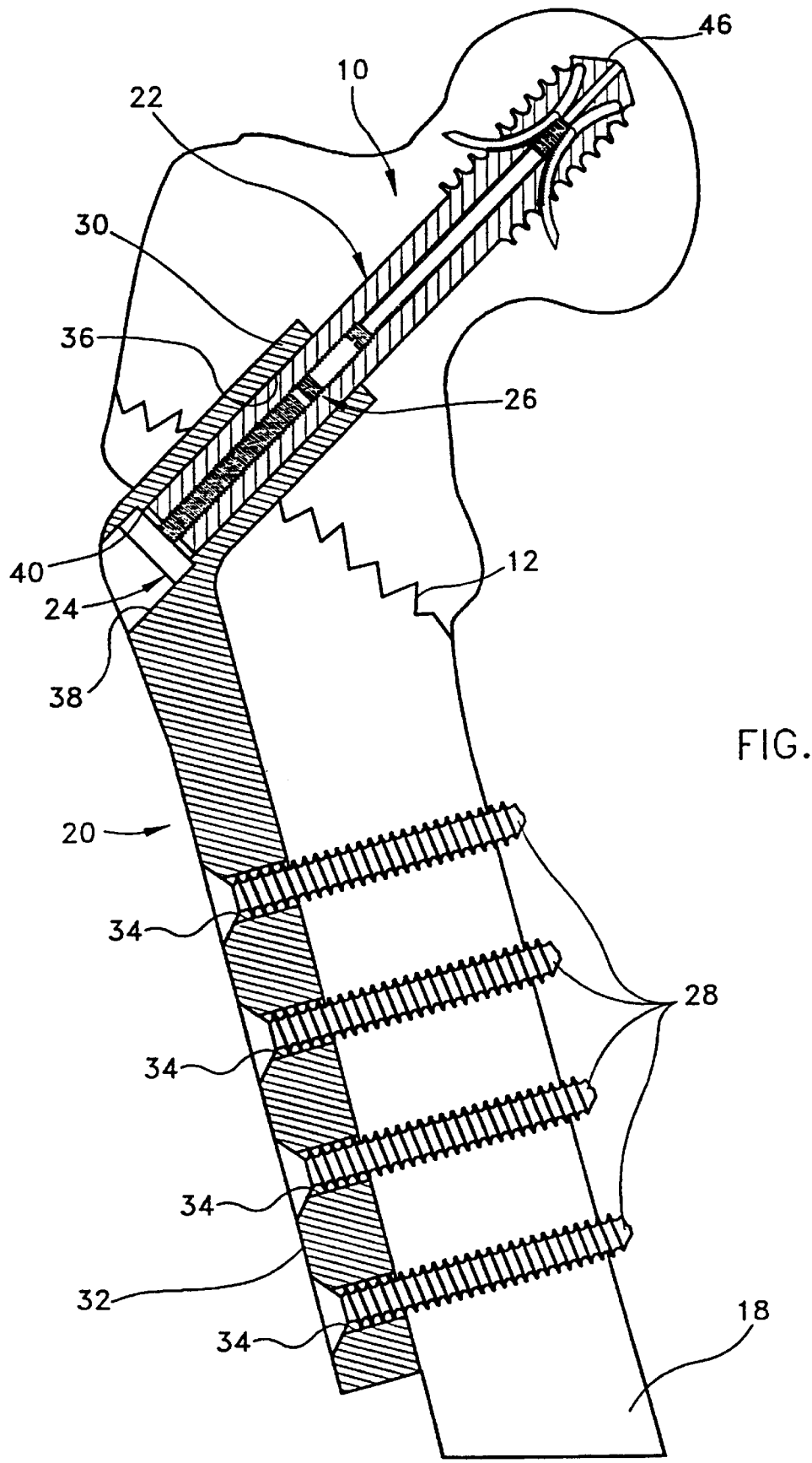
FIG. 2 is an enlarged view, partly in section, of the apparatus of the present invention shown in FIG. 1.
Figure 10:
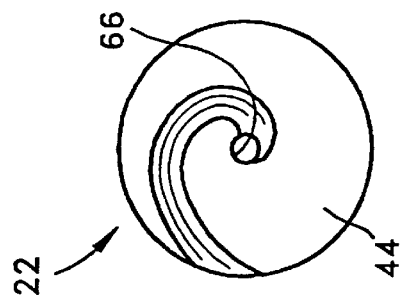
FIG. 10 is another end view of the present invention.
Figure 7:
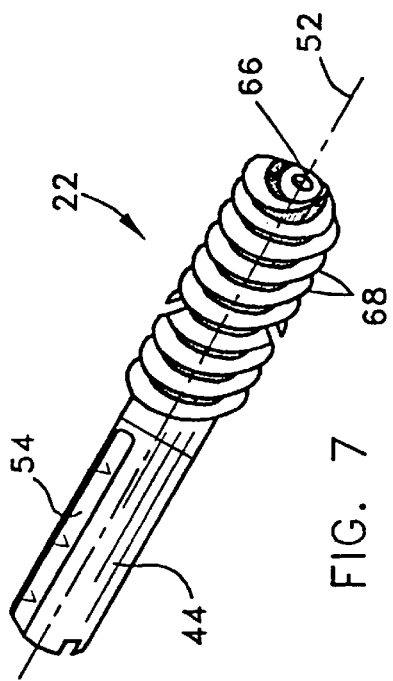
FIG. 7 is a perspective view of the fastener illustrated in FIGS. 5 and 6.

As shown, the surgical fastener assembly 10 includes a guide, generally represented by reference numeral 20 and an elongated anchor, generally represented by reference numeral 22. As shown in FIG. 2, the surgical anchor assembly 10 further includes a compression screw or fastener 24 and a retainer 26 for releasably locking the fastener 24 against rotation. As shown in FIG. 2, a series of screws 28 operate in combination with and serve to secure the guide 20 to the bone section 18.

As shown in FIGS. 2 through 4, guide 20 includes a hollow sleeve 30 that is rigidly attached to a trochanteric plate 32 at the proper angle. The proximal portion 14 of the bone 18 is bored so as to receive the sleeve 30. The distal portion 16 of the bone 18 is configuratively manipulated to accommodate an end portion of the sleeve 30 therewithin. As shown, the plate 32 is provided with a plurality of throughholes 34 that allow the screws 28 to pass endwise therethrough, thereby securing the guide 20 to the bone section 18. The sleeve 30 defines a throughbore 36 that is open at opposite ends thereof. In a preferred form of the invention, the guide 20 is formed from a material chosen from the class comprised of: titanium, a titanium alloy, stainless steel, or cobalt chromium alloy.

Notably, the throughbore 36 is provided with a counterbore 38 at one end thereof. In the illustrated embodiment, the counterbore 38 has a larger diameter than does the throughbore 36. Accordingly, an annular or radial step 40 is defined toward one end of the throughbore 36.

As shown in FIG. 4, the anchor 22 includes an elongated insert 44 preferably formed from a material chosen from the class comprised of: titanium, a titanium alloy, stainless steel or cobalt chromium alloy. The insert 44 has opposed first and second axially aligned ends 46 and 48, respectively. The insert 44 is sized such that when inserted within the bone, the first end 46 is disposed on to one side of the fracture line 12 while the second end 48 of insert 44 is disposed on an opposite side of the fracture line 12. Notably, cooperative instrumentalities 50 are defined on the sleeve 30 of guide 20 and on insert 44. The purpose of the cooperative instrumentalities 50 is to allow for axial movement of the sleeve 30 along an axis 52 defined by the insert 44 while preventing rotational movement of the sleeve 30 relative to the anchor 22.

In the illustrated embodiment, and as well known, the cooperative instrumentalities 50 preferably comprises a pair of flats 54 extending axially along and inwardly from the second end 48 of insert 44. The flats 54 are diametrically opposed and generally parallel to each other. As shown in FIG. 3, the throughbore 36 of sleeve 30 includes generally flat sides 56 that are arranged in opposed and generally parallel relationship relative to each other. The flat sides 56 of bore 36 to allow the second end 48 of the insert to slidably move therewithin while the flats 54 cooperate with the flat sides 56 in preventing rotation of the sleeve 30 and, thereby, the guide 20 relative to the anchor 22. It will be appreciated, and it is within the spirit and scope of the present invention that other forms of cooperative instrumentalities for allowing endwise axial movement of the anchor 22 relative to the guide 20 while preventing rotational movement therebetween would equally suffice.

As shown in FIGS. 5 and 6, the anchor 22 of the surgical fastener assembly 10 further includes a series of elongated pins 60 operably associated toward the first end 46 of the insert 44 for movement between a retracted position (FIG. 5) and a radially extended position (FIG. 6). As shown, the pins 60 are carried by the insert 44 for endwise and radial displacement relative thereto. In the illustrated embodiment of the invention, four pins 60 are equidistantly spaced relative to each other for positive endwise movement in opposite directions between the retracted and extended positions shown in FIGS. 5 and 6, respectively.

A salient feature of the present invention relates to the provision of a mechanism 64 for positively positioning the pins 60 relative to the surgical anchor 22. That is, and as will be described in detail below, the purpose of mechanism 64 is to positively extend the pins 60 radially outwardly from the insert 44, thereby enhancing securement of the anchor 22 within the bone (FIG. 1). Additionally, and in response to mechanical manipulation, the mechanism 64 furthermore operates to positively retract the pins 60 into the surgical anchor 22, thereby facilitating surgical removal of the anchor 22 when desired or when found to be surgically necessary.

Turning to FIGS. 7 through 10, insert 44 of anchor 22 defines an elongated bore 66 preferably arranged coaxially about the longitudinal axis 52 and opening to the first and second ends 46 and 48, respectively, of the insert 44. As shown, the first end 46 of the fastener 44 is preferably pointed to facilitate insertion of the fastener 44 into the bone.

As will be appreciated by those skilled in the art, the exterior configuration of the insert 44 can take a myriad of shapes and forms. According the present invention, and as illustrated in FIGS. 7 through 10, the elongated insert 44 preferably has external threading 68 axially extending therealong and leading rearwardly from the pointed first end 46. As mentioned, the pointed configuration of the insert 44 promotes insertion and, in the illustrated embodiment, self tapping of the anchor 22 within the substance of the bone. The external threading 68 along the exterior of insert 44 has a relatively coarse pitch to enhance the purchasing ability and the anchorage of the anchor 22 within the substance of the bone in response to turning movements being imparted to the anchor 22.

Figure 9:
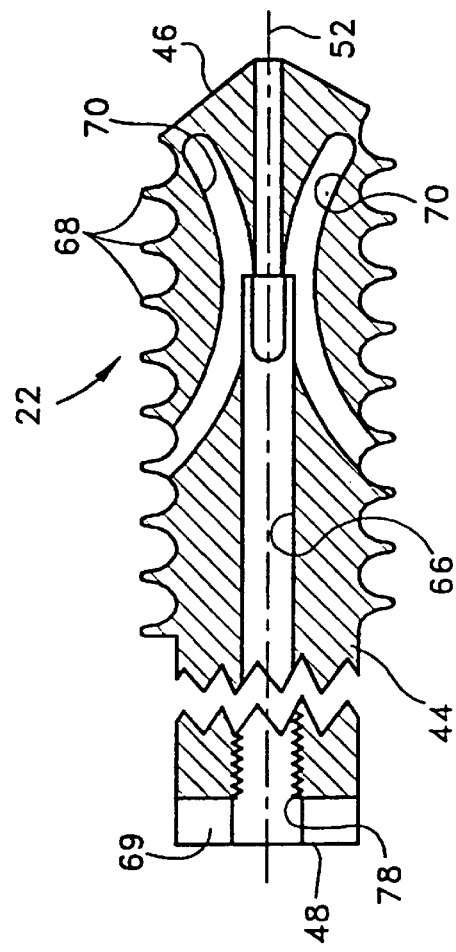
FIG. 9 is a sectional view taken along line 9—9 of FIG. 8.
Figure 8:
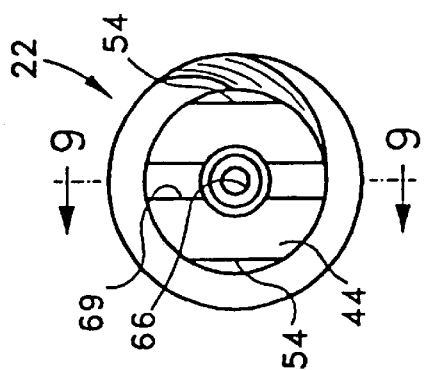
FIG. 8 is an end view of the fastener as shown in FIG. 7.
Figure 13:
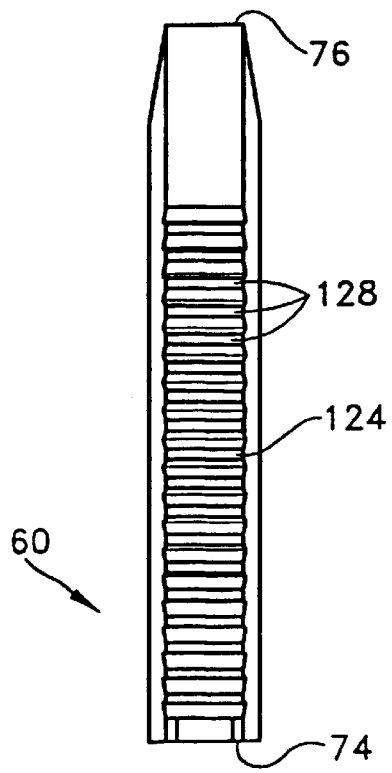
FIG. 13 is another side elevational view of the pin or barb illustrated in FIG. 11.
Figure 12:
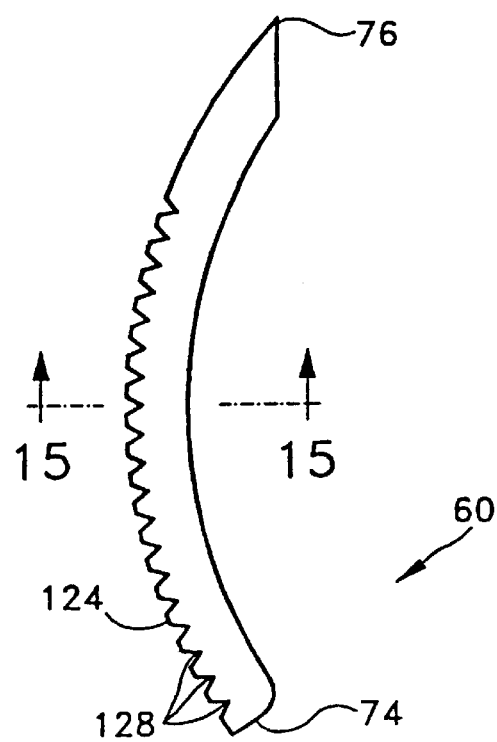
FIG. 12 is a side elevational view of the pin illustrated in FIG. 11.
Figure 14:
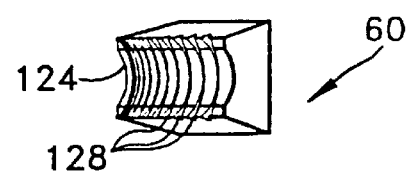
FIG. 14 is an end view of the pin or barb illustrated in FIG. 12.
Figure 11:
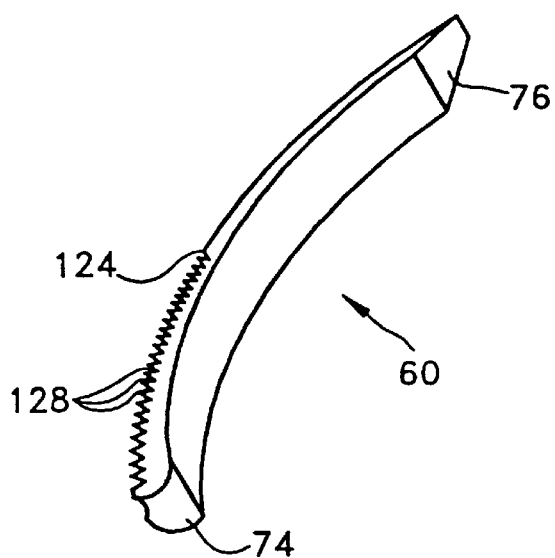
FIG. 11 is an enlarged perspective view of a pin or barb forming part of the first embodiment of the surgical fastener assembly according to the present invention.
Figure 15:
FIG. 15 is a sectional view taken along line 15—15 of FIG. 12.
Figure 16:
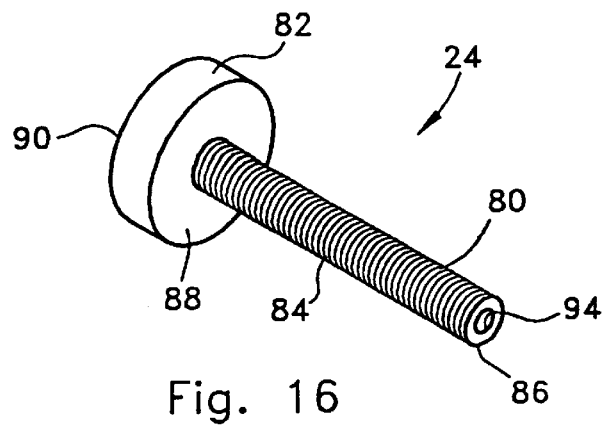
FIG. 16 is a perspective view of one form of a compression screw forming part of the present invention.

As shown in FIG. 9, the second or trailing end 48 of the insert 44 is preferably configured to releasably accommodate a driving tool (not shown) capable of imparting turning movements to the anchor 22. In a preferred form, and as shown in FIGS. 8 and 9, the trailing or second end of the insert 44 is suitably configured with a slot-like opening 69 for releasably accommodating a distal end of a driving tool. It will be appreciated, however, that any suitable configuration including a socket-like configuration would equally suffice without detracting or departing from the spirit and scope of the present invention.

As shown in FIG. 9, the insert 44 further defines a series of axially elongated openings arranged in spaced circumferential relation relative to each other. In the illustrated form of the invention, insert 44 is provided with four openings 70. Since the openings 70 are all substantially similar, only one opening 70 will be described in detail with the understanding that the other openings in the insert are similar thereto. Each opening 70, intermediate positive ends thereof, intersects with and opens to the elongated bore 66 defined by insert 44. Preferably, each elongated opening 70 has a blind configuration but opens at one end to the exterior of the insert 44. As will be appreciated, the openings 70 are generally equally disposed about the axis 52 of insert 44. In the form of the invention illustrated in FIG. 9, each elongated opening 70 has a curvilinear or arcuate configuration between opposite ends thereof. That is, in the illustrated form of the invention, each opening 70 has an arcuate configuration having a predetermined and substantially constant radius.

An exemplary form of pin 60 is illustrated in FIGS. 11 through 15. Each pin 60 is shaped to slidably fit endwise within a respective one of the openings 70 formed in the insert 44. The shape and size of each pin 60 generally corresponds to the shape and size of an opening 70 defined by the insert 44. Preferably, each pin 60 is formed from a substantially rigid material that is biocompatible with the bone tissue of human beings. That is, the pins 60 should be configured with sufficient strength so as to allow for insertion in and through the bone tissue without substantially bending intermediate opposite ends thereof. In a most preferred form of the invention, each pin 60 is formed from a material selected from the class comprised of: titanium, a titanium alloy, stainless steel, or a cobalt chromium alloy.

In the embodiment illustrated in FIGS. 11 through 15, each pin 60 has a leading end 74 and an opposite generally pointed end 76. Intermediate its ends, each pin 60 preferably has a curvilinear or arcuate configuration. In the illustrated form of the invention, each pin 60 has a curved arc with a predetermined radius that is substantially equal to the predetermined radius of each opening 70 formed in insert 44 (FIG. 9) and which extends proximate to and outwardly away from the axis 52 of insert 44.

In a most preferred form of the invention, each pin 60 preferably forms an arc of about 80 degrees between opposite ends thereof, and with the length of each pin 60 being selected such that when the leading end 74 of the pin 60 is fully retracted within the fastener (FIG. 5), the opposite pointed end 76 of the pin or barb 60 will be positioned within the outside diameter of the insert 44 (FIG. 5) to facilitate insertion of the surgical anchor 20 within the bone of the patient. Moreover, it is to be appreciated that the length of each barb or pin 60 is sized such that when the pins 60 are displaced to their extended position (FIG. 6) the leading end 74 of each pin 60 remains operably associated with the mechanism 64 to allow for positive retraction of the pins 60 from their extended positions when desired or found necessary by the surgeon.

The compressive and cannulated fastener 24 as schematically illustrated in FIGS. 16 through 20. The purpose of the cannulated fastener 24 is to maintain the bone fragments (FIG. 1) in adjustable compressive relationship relative to each other as by axially fixing the guide 20 to the anchor 22 (FIG. 2).

Returning to FIGS. 5, 6 and 9, the elongated bore 66 of the insert 44 opens to the second or trailing end 48 thereof. The bore 66 defines an internally threaded portion 78 extending inwardly from the second or trailing end 48 of the insert 44. Preferably, the internally threaded portion 78 of bore 66 has a relatively fine pitched threading extending there along.

The compressive and cannulated fastener 24 is schematically illustrated in FIGS. 16 through 20. The purpose of the cannulated fastener 24 is to maintain the bone fragments (FIG. 1) in adjustable compressive relationship relative to each other as by axially fixing the guide 20 to the anchor 22 (FIG. 2) such that the guide 20 is prevented from axially moving away from the anchor 22, but allows movement of guide 20 toward the pointed or first end 46 of the anchor 22 (FIG. 2).

Fastener 24 is preferably formed from a material that is biocompatible with bone tissue or a substance and is preferably selected from the class comprised of: titanium, a titanium alloy, stainless steel, or a cobalt chromium alloy. As will be appreciated, and although not specifically mentioned herein, other unnamed materials may well equally suffice without detracting or departing from the spirit and scope of the present invention.

As shown, the fastener 24 is provided with an elongated shank portion 80 and an enlarged head portion 82. The shank portion 80 of fastener 24 is provided with external threading 84 extending axially from a leading end 86 of the fastener 24. The external threading 84 has a relatively fine pitch that corresponds to the threading extending internally along the threaded portion 78 of anchor 22. The enlarged head portion 82 of fastener 24 has a diameter slightly smaller than the diameter of the counterbore 38 defined by the insert 44 (FIG. 2). As will be appreciated from an understanding of the present invention, the axial length of the head portion 82 can be altered from that illustrated without detracting or departing from the spirit and scope of the present invention. That is, during a surgery, surgeon may have a collection of different fasteners 24 to select from; with each anchor having a different length such that a proper relationship is maintained between the guide 20 and anchor 22. Notably, the enlarged head portion 82 defines a radial shoulder 88 relative to the shank portion 80.

Figures 17, 18, 19:
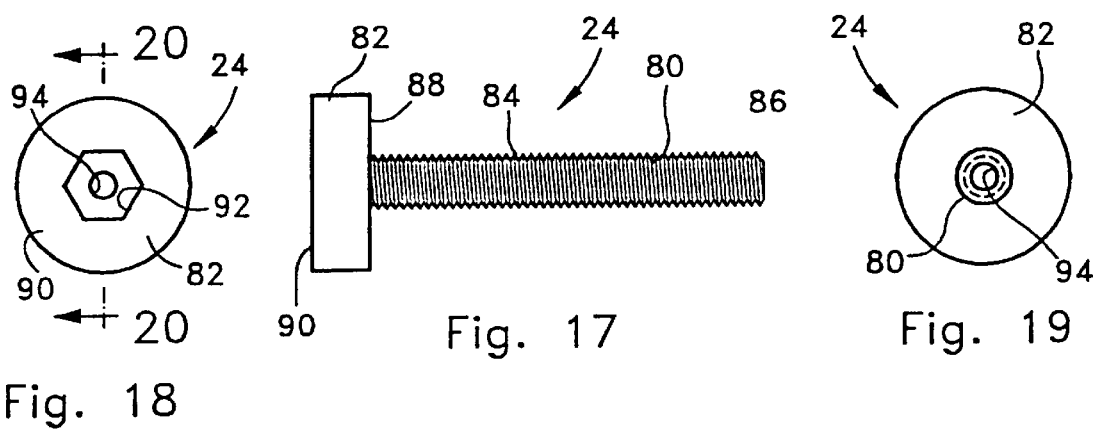
FIG. 17 is a side elevational view of the compression screw illustrated in FIG. 16.
FIG. 18 is a left end view of the compression screw illustrated in FIG. 17.
FIG. 19 is a right end view of the compression screw illustrated in FIG. 17.
Figure 20:
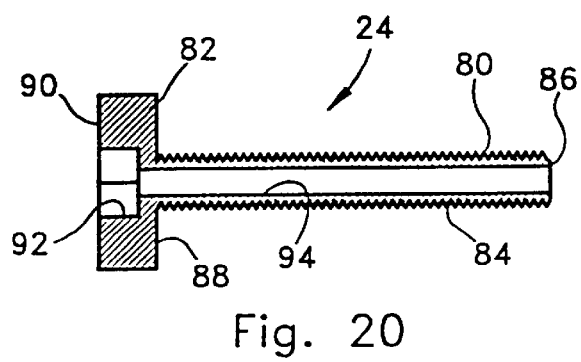
FIG. 20 is a sectional view taken along line 20—20 of FIG. 18.
Figure 21:
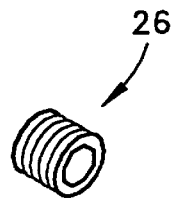
FIG. 21 is a perspective view of a retainer forming part of the anchor assembly illustrated in FIG. 2.

As shown in FIGS. 18 and 20, a trailing end 90 of the fastener 24 is preferably configured to releasably accommodate a driving tool (not shown) capable of imparting turning movements to the fastener 24. In a preferred form, and as shown in FIGS. 18 and 20, the trailing end 90 of fastener 24 is configured with a socket-like opening 92 for releasably accommodating a distal end of a driving tool. In a most preferred form of the invention, and as shown, the socket or opening 92 has a hexagonal-like cross sectional configuration. It will be appreciated, however, that any suitable configuration including an elongated slot would equally suffice without detracting or departing from the spirit and scope of the present invention. The cannulated fastener 24 furthermore defines an elongated bore 94 that opens to the leading and trailing ends 86 and 90, respectively, of the fastener.

In the illustrated embodiment shown in FIG. 2, the anchor 22 is fastened within the bone fragment to one side of the fracture line 12. As mentioned, anchor 22 is configured such that the opposite or second end 48 of the anchor 22 extends to an opposite side of the fracture line 12. Thereafter, the guide 20 is arranged in cooperative relationship relative to the anchor 22. As shown, the sleeve 30 of guide 20 slidably fits endwise over and telescopically along the free end of the anchor 22. The screws 28 are used to fasten the plate 32 of guide 20 to the bone 18. It will be observed that the cannulated compressive fastener 24 is thereafter arranged in operable combination with the anchor 22 and guide 20. That is, the leading end 86 of the compressive screw 24 is inserted through the bore 36 of the sleeve 30 in turn such that the external threading 84 extending there along operably engages with the internal threading 78 at the proximal end of the anchor 22. Continued rotation of the fastener 24, ultimately, will cause the radial shoulder 88 on the enlarged head portion 82 to engage the radial stop 40 defined by the counterbore 38 and the guide 20. As will be appreciated, continued rotation of the screw 24 will cause the bone fragments to be brought into compressive relationship relative to each other. The compressive screw 24 furthermore allows the surgeon the appropriate "feel" as the screw is tightened, thus bringing the bone fragments into compressive relationship relative to each other.

One form of a retainer 26 is schematically illustrated in FIGS. 21 through 25. As shown, retainer 26 has external threading 100 extending axially there along between leading and trailing ends 102 and 104, respectively thereof. The retainer 26 is preferably formed from a material that is biocompatible with bone tissue or substance and is preferably ultra-high molecular weight polyethylene. It should be appreciated, however, that other unnamed materials would equally suffice without detracting or departing from the spirit and scope of the present invention. Notably, the external threading 100 extending along the outside of retainer 26 has a fine pitch thereto which corresponds to the threading extending along the internally threaded portion 78 of the insert 44.

Figure 25:
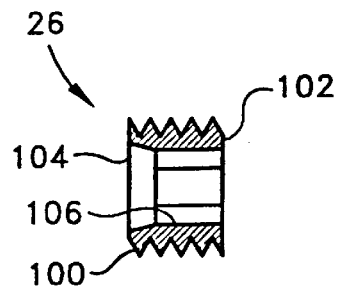
FIG. 25 is a sectional view taken along line 25—25 of FIG. 23.
Figure 23:
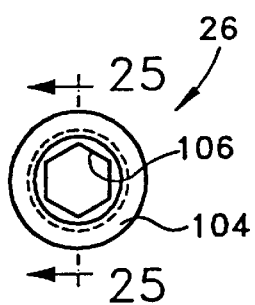
FIG. 23 is a left end view of the retainer illustrated in FIG. 22.
Figure 22:
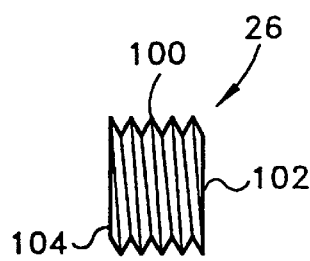
FIG. 22 is a side elevational view of the retainer illustrated in FIG. 21.
Figure 24:
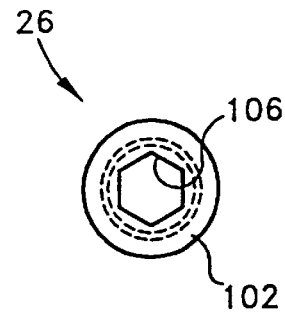
FIG. 24 is a right end view of the retainer shown in FIG. 22.
Figure 26:
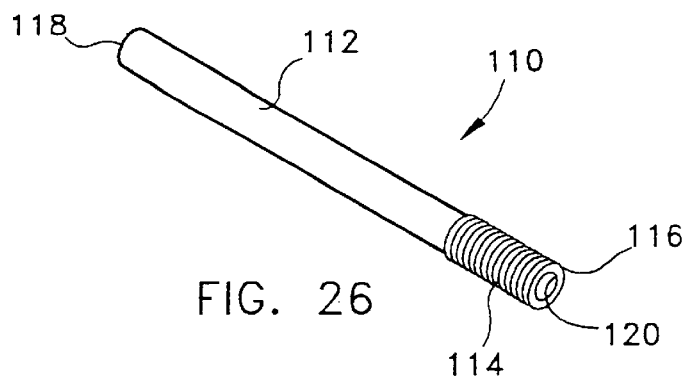
FIG. 26 is a perspective view of a driver forming part of the first embodiment of this surgical fastener assembly according to the present invention.

As shown in FIGS. 23, 24 and 25, the retainer 26 is provided with a throughbore 106 that opens to opposite ends 102 and 104 of the retainer. In a preferred form, and as shown in FIGS. 23, 24 and 25, a lengthwise portion of the throughbore 106 has a hexagonal-like cross sectional configuration for releasably accommodating a distal end of the driving tool. It will be appreciated, however, that any suitable socket-like configuration other than hexagonal would equally suffice without detracting or departing from the spirit and scope of the present invention.

During assembly of the surgical fastener assembly 10, and as shown in FIG. 25A, the retainer 26 is initially threaded into the internally threaded portion 78 of the anchor 22. Thereafter, and in the manner described above, the compressive fastener 24 is operably associated with the anchor 22. After the compressive relationship between the guide 20 and anchor 22 has been established, as a result of turning the compressive screw 24, a suitably elongated tool 95 is passed through the bore 94 (FIG. 20) of the cannulated fastener 24 and into releasable engagement with the socket-like configuration defined in the throughbore 106 of retainer 26.

As shown in FIG. 25B, appropriate rotation of the retainer 26 under the influence of tool 95 will thereafter cause the trailing end 104 to be moved into abutting relationship to the leading end 86 of the compressive screw 24, thereby locking the compressive screw 24 and, thus, maintaining the compressive relationship between the bone fragments. As will be appreciated, however, the bone fragments are allowed to shift through the axial movement of the head portion 82 along the length of the counterbore 38. The head portion 82 of the compressive screw 24 limits, however, movement of the anchor 22 and the bone fragments secured thereby away from the bone 18, thereby maintaining the compressive relationship therebetween.

The mechanism 64 for positively displacing the pins 60 in opposite directions between retracted and extended positions (FIGS. 5 and 6, respectively) will now be described. As will be appreciated, the mechanism for positively displacing the pins 60 in opposite directions can take a myriad of different forms without detracting or departing from the spirit and scope of the present invention. One mechanism which has proven advantageous and quite effective involves equipping the anchor 20 with a manually operated driver 110 (FIGS. 5 and 6) which is operably associated with the pins 60 such that upon manipulation of the driver 110 the pins 60 will endwise be displaced relative to the anchor 22, thereby effecting the anchorage of the surgical anchor 22 within the bone.

Figures 27, 28, 29:
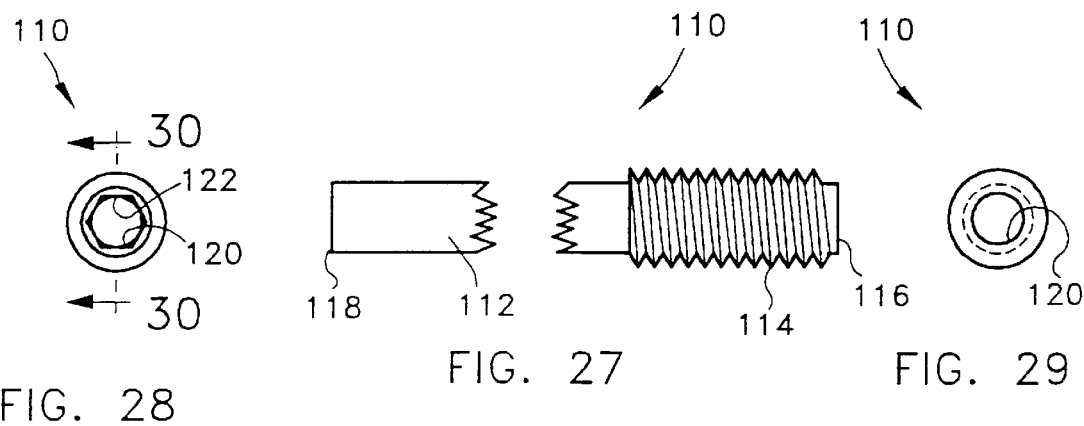
FIG. 27 is a fragmentary side elevational view of the driver illustrated in FIG. 26.
FIG. 28 is a left end view of the driver illustrated in FIG. 27.
FIG. 29 is a right end view of the driver illustrated in FIG. 27.
Figure 30:
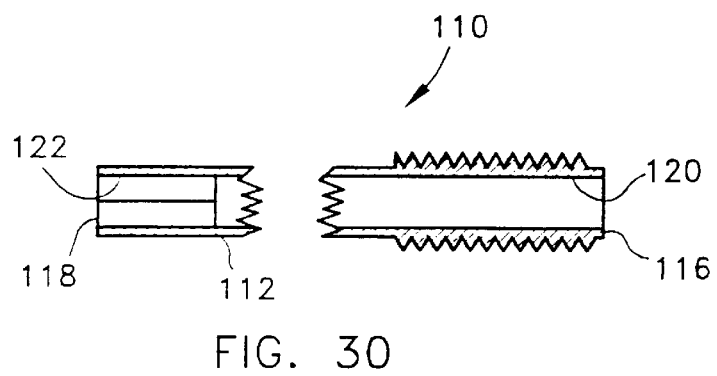
FIG. 30 is a longitudinal sectional view taken along line 30—30 of FIG. 28.

FIGS. 26 through 30 illustrate one form of a driver 110 for axially and appositively displacing the pins 60 (FIGS. 5 and 6) of the surgical anchor in opposite directions. As shown, driver 110 comprises an axially elongated member 112 having external threading 114 extending axially rearwardly from a leading end 116 toward a trailing end 118. The driver member 112 is formed from a material that is biocompatible with bone tissue or a substance that is preferably selected from the class comprised of: titanium, a titanium alloy, stainless steel, or a cobalt chromium alloy. It should be appreciated, however, other unnamed materials would equally suffice without detracting or departing from the spirit and scope of the present invention. The outside diameter of the threading 114 of member 112 is such that it slidably fits endwise through the elongated bore 66 defined by insert 44 (FIGS. 5 and 6) and is accommodated for free turning movements in either rotational direction within the bore 66 of insert 44. Preferably, the external threading 114 on member 112 has a relatively fine pitch thereto. As shown in FIGS. 26, 28, 29 and 30, the member 112 preferably has an elongated bore 120 that opens to the leading and trailing ends 116 and 118 of member 112. The trailing end 118 of the member 112 is preferably configured to releasably accommodate a driving tool (not shown) capable of imparting turning movements to the driver 110. In a preferred form, and as shown in FIGS. 28 and 30, the trailing end 118 of member 112 is suitably configured with a socket-like opening 122 for releasably accommodating the distal end of a driving tool. In a most preferred form of the invention, and as shown in FIGS. 28 and 30, the socket or opening 122 has a hexagonal-like cross sectional configuration. It will be appreciated, however, that any suitable configuration, including a square or triangular configuration would equally suffice without detracting or departing from the spirit and scope of the present invention.

As will be described hereinafter in detail below, the driver 110 of mechanism 64 is operably associated with each pin 60 such that manipulation of the driver 110 results in positive endwise displacement of the pins 60 either toward an extended or retracted position depending upon the movements provided to the driver 110 of mechanism 64. In the illustrated form of the invention and returning to FIGS. 11 through 15, each pin or barb 60 preferably has an inner surface 124, which proximates the axis 52 (FIGS. 7 and 9) of the anchor 22 when the pins 60 are inserted within the insert 44, and an outer surface 126. As shown, in FIGS. 11 through 15, the inner surface 124 of each pin 60 has a series of vertically spaced serrations 128 thereon. The serrations 128 extend axially rearwardly from the leading end 74 and for a lengthwise distance toward the pointed end 76 of each pin 60. Notably, the serrations 128 on each pin 60 are configured for threadable engagement with the exterior threading 114 extending axially along the outer surface of driver 110. As such, the driver 110 is operably engaged or associated with each of the pins 60 of this surgical anchor assembly.

Figure 31:
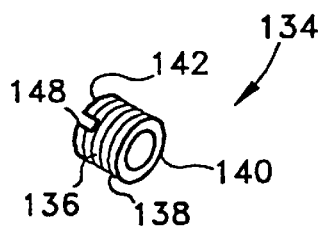
FIG. 31 is a perspective view of a limit stop forming part of the first embodiment of the present invention.
Figure 35:
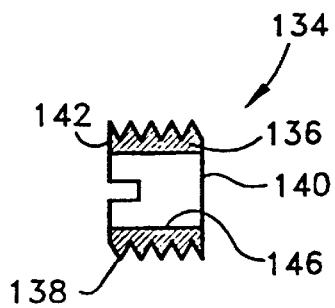
FIG. 35 is a sectional view taken along line 35—35 of FIG. 33.
Figure 33:
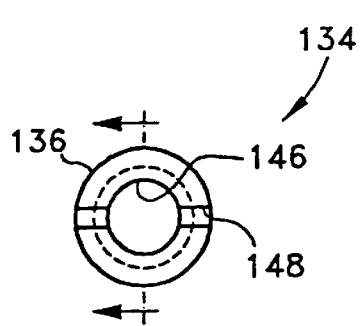
FIG. 33 is a left end elevational view of the limit stop illustrated in FIG. 32.
Figure 32:
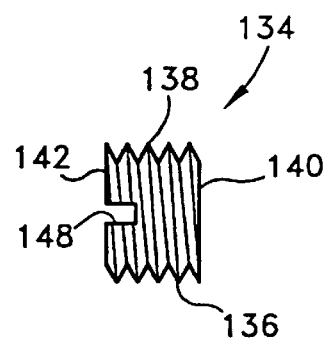
FIG. 32 is an enlarged side elevational view of the limit stop illustrated in FIG. 31.
Figure 34:
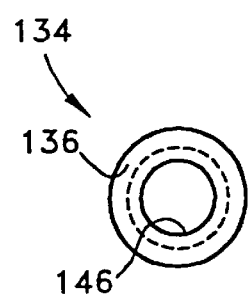
FIG. 34 is a right end view of the limit stop illustrated in FIG. 32.

As shown in FIGS. 5 and 6, mechanism 64 for positively displacing the pins 60 between retracted and extended positions and vice-versa, further includes a limit stop 134 for preventing axial displacement of the driver 110 when rotated. One form of limit stop 134 is illustrated in FIGS. 31 through 35. Preferably, the limit stop 134 is formed from a material that is biocompatible with human bone tissue. In a most preferred form of the invention, the limit stop 134 is formed from a material chosen from the class comprised of: titanium, a titanium alloy, stainless steel, or a cobalt chromium alloy. It will be appreciated, however, that other materials would equally suffice without detracting or departing from the spirit and scope of the present invention. As shown in FIGS. 31 through 35, the limit stop 134 preferably includes a hollow member 136 with external threading 138 extending between leading and trailing ends 140 and 142, respectively, thereof. The external threading 138 has a relatively fine pitch which corresponds to the threading extending along the internally threaded portion 78 of insert 44 at the second end 48 of anchor 22. The trailing end 142 of the limit stop 134 is preferably configured to releasably accommodate a driving tool (not shown) capable of imparting turning movements to the limit stop 134. In a preferred form, and as shown in FIGS. 31, 32 and 33, the trailing end 142 of limit stop 134 is provided with an elongated slot 144 for releasably accommodating a distal end of the driving tool. Moreover, the limit stop 134 defines a throughbore 146 that opens to leading and trailing ends 140 and 142, respectively, of the limit stop and thereby allowing a tool to be passed endwise therethrough into operable engagement with the driver 10.

Figure 36:
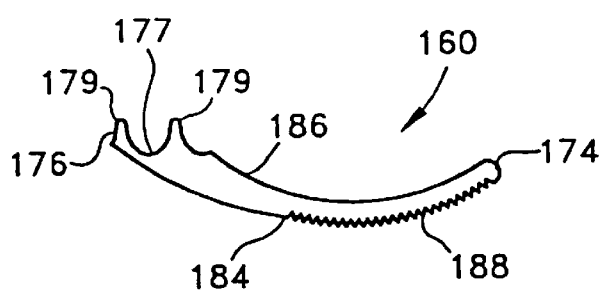
FIG. 36 is a view similar to FIG. 12 but showing an alternative form of pin or barb according to the present invention.
Figure 37:
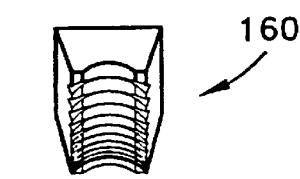
FIG. 37 is an enlarged right end elevational view of the pin or barb illustrated in FIG. 36.

An alternative form of pin 160 to be arranged in operable combination with the anchor 22 as shown in FIGS. 36 and 37. Pin 160 is substantially similar to pin 60 illustrated in FIGS. 11 through 15 and described in detail above. In the embodiment illustrated in FIGS. 36 and 37, each pin 160 has a leading end 174 and an opposite end 176. Intermediate its ends, each pin 160 preferably has a curvilinear or arcuate configuration. In the illustrated form of the invention, each pin has a curved arc with a predetermined radius that is substantially equal to the predetermined radius of each opening 170 formed in an insert 144 as shown in FIG. 38.

In the embodiment of the pin shown in FIG. 36, each pin 160 preferably forms an arc of about 80° between opposite ends thereof, and with the length of each pin being selected such that when the leading end 174 of the pin 160 is fully retracted within the fastener or anchor 22, the opposite end 176 of the pin or barb 160 will be positioned within the outside diameter of the insert 144.

In the illustrated embodiment shown, end 176 of each pin 160 is formed with a configuration that complements the order configuration of the anchor or fastener 22. In the illustrated embodiment the end 176 of each pin 160 is formed with a channel 177 disposed between two substantially similar projections 179. As shown in FIG. 38, when the pin 160 is fully retracted the channel-like configuration and the projections 179 on opposite sides thereof blend into the outer threaded configuration extending axially along the fastener 22. It is to be appreciated that the length of each barb or pin 160 is sized such that when the pins 160 are displaced to their extended position, as shown in FIG. 39, the leading end 174 of each pin 160 remains operably associated with the mechanism 64 to allow for positive retraction of the pins 160 from their extended positions when desired or found necessary by the surgeon.

Figure 38:
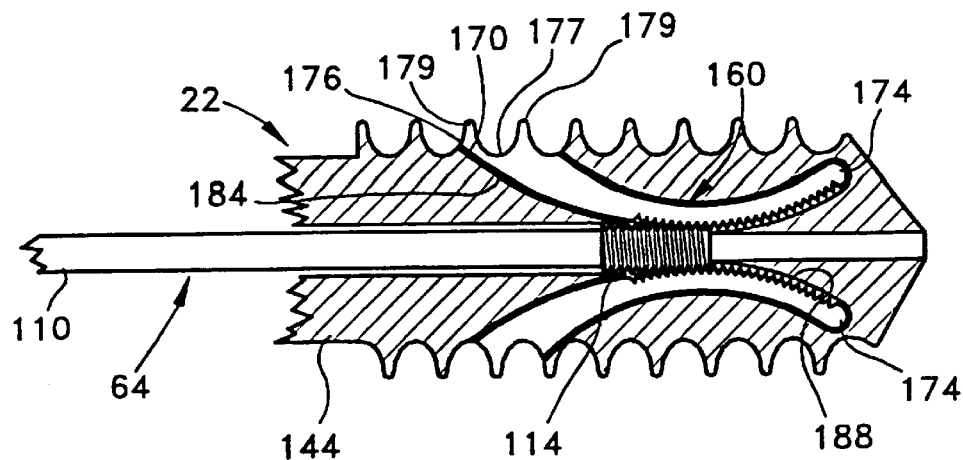
FIG. 38 is a view similar to FIG. 5 showing the alternative form of pins or barbs arranged in combination with the insert and in retracted positions relative thereto.
Figure 39:
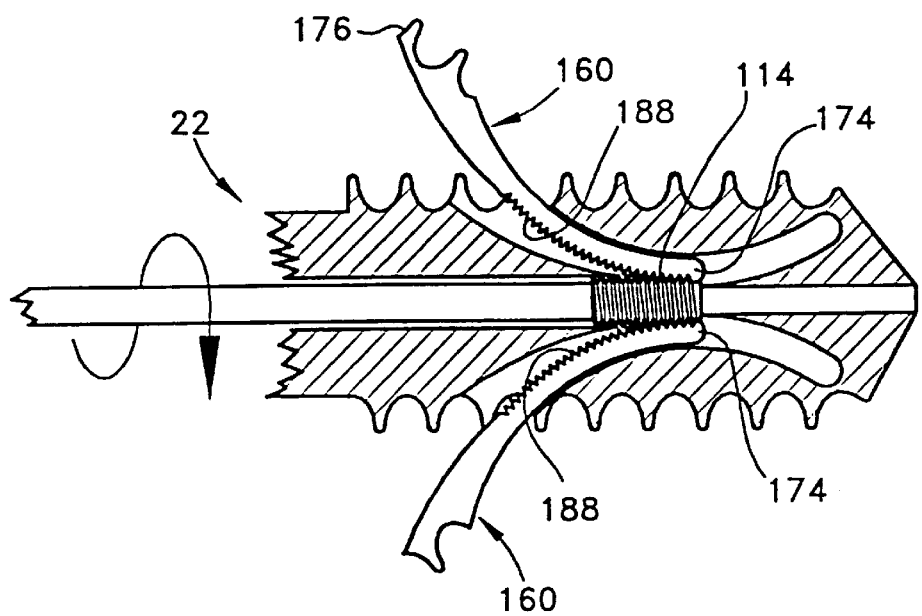
FIG. 39 is a view similar to FIG. 38 but showing the alternative form of fasteners in an extended position relative to the fastener.

As shown in FIG. 36, each pin or barb 160 preferably has an inner surface 184 which, as illustrated in FIGS. 38 and 39, proximates the axis 52 of the anchor when the pins are inserted within the insert 144 and an outer surface 186. The inner surface 184 of each pin has a series of spaced serrations 188 that extend axially rearwardly from the leading end 174 and for a lengthwise distance toward the second or other end 176 of each pin 160. The serrations 188 on each pin are configured for threadable engagement with the exterior threading 114 extending axially along the outer surface of driver 110 of mechanism 64 as described in detail above. As such, the driver 110 is operably engaged or associated with each of the pins 160 of this surgical anchor assembly.

Figure 41:
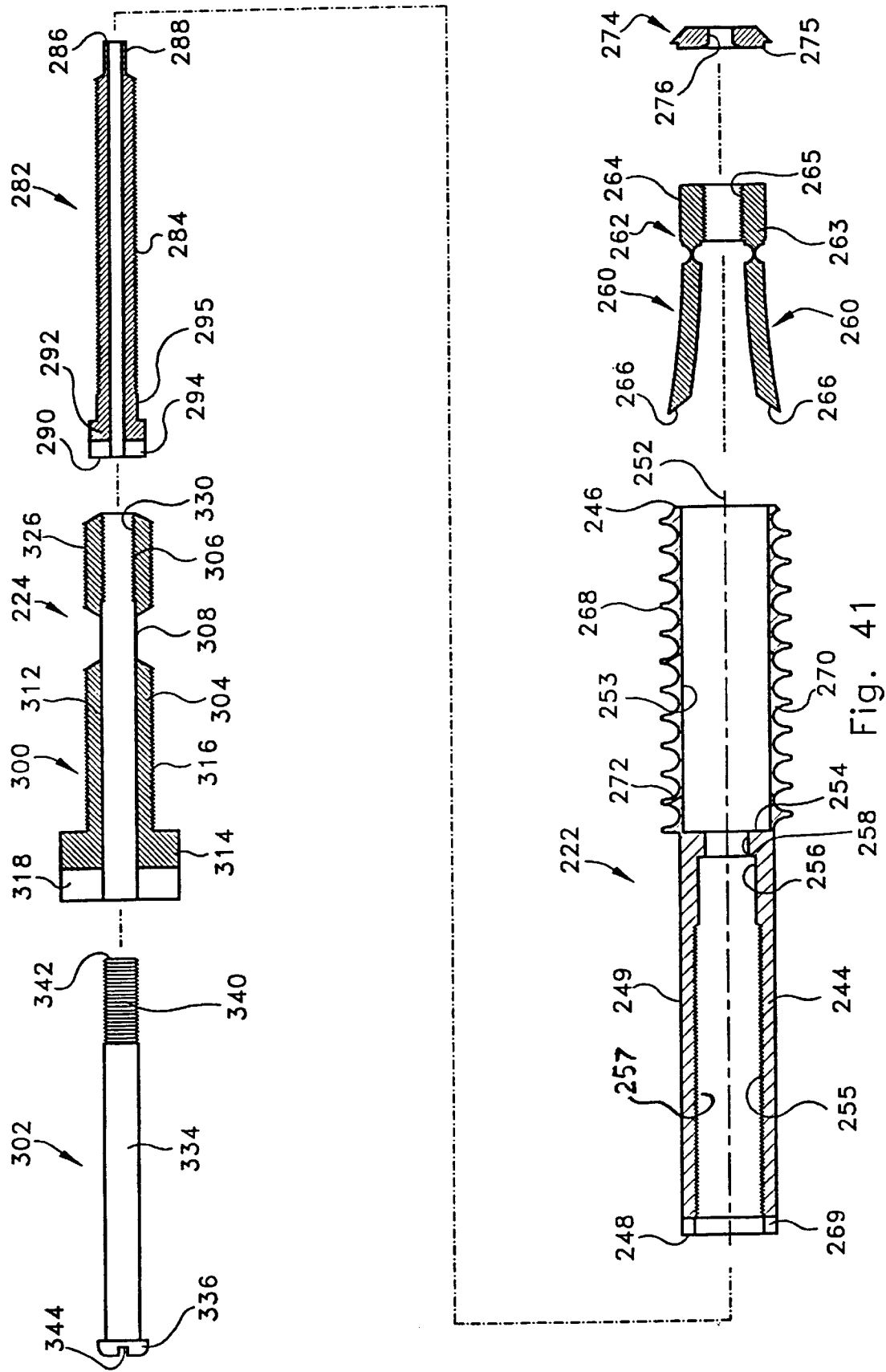
FIG. 41 is a longitudinal sectional view showing the components of the second embodiment of the present invention in exploded or disassembled relationship relative to each other.
Figure 54:
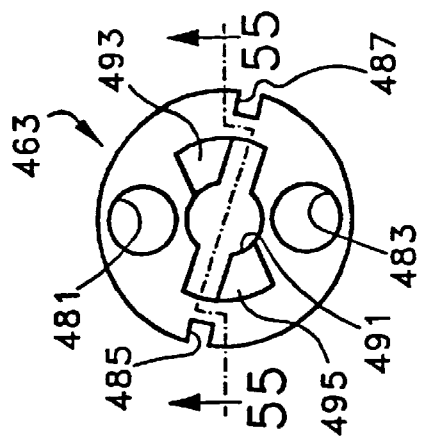
FIG. 54 is a right end view of the slide illustrated in FIG. 52.
Figure 55:
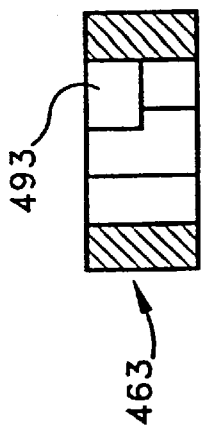
FIG. 55 is a sectional view taken along line 55—55 of FIG. 54.
Figure 52:
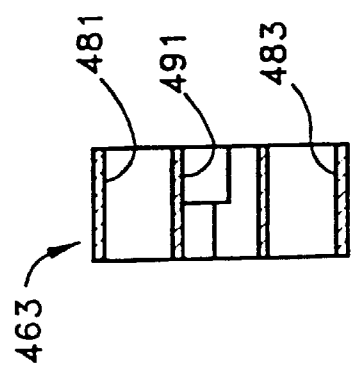
FIG. 52 is a sectional view of a slide forming a component part of the third embodiment of the present invention.
Figure 53:
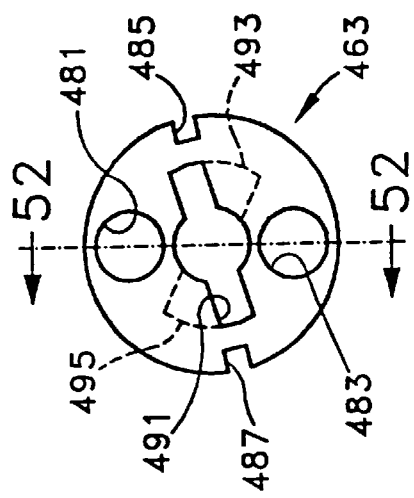
FIG. 53 is a left end view of the slide illustrated in FIG. 52.

FIG. 40 schematically illustrates an alternative form for the surgical anchor assembly. This alternative form of the surgical anchor assembly is generally represented by reference numeral 210. As shown in FIG. 40, the surgical anchor assembly 210 includes a guide, generally represented by reference numeral 220 and an elongated anchor, generally represented by reference numeral 222. As shown in FIG. 41, and as will be discussed in detail below, the surgical fastener assembly 210 further includes a compressive fastener assembly 224 for holding the guide 220 in compressor relationship relative to the anchor 222.

The guide 220 is substantially similar to the guide 20 described in detail above and, thus, a detailed description need not be provided therefor. Suffice it to say, the guide 220 includes a hollow sleeve 230 that is substantially similar to the sleeve 30 discussed above. Sleeve 230 defines a throughbore 236 that is open at opposite ends thereof. The throughbore is provided with a counterbore portion 238 at one end thereof. In the illustrated embodiment, the counterbore 238 has a larger diameter than does the throughbore 236 and, thus, an annular or radial step 240 is defined therebetween.

The anchor 222 includes an elongated insert 244 having opposed first and second ends 246 and 248. The insert 244 is preferably formed from a material similar to that used to form insert 44. Insert 244 is sized such that when inserted within the bone, the first end 246 is disposed to one side of a fracture line while the second end 248 of the insert 244 is disposed to an opposite side of the fracture line.

As shown in FIG. 40, the anchor 222 of the surgical fastener assembly 210 further includes a series of elongated pins or barbs 260 operably associated toward the first end 246 of the insert 244 for movement between a retracted position (FIG. 40) and a radially extended position (FIG. 42). As shown, the pins 260 are carried by the insert 244 for endwise and radial displacement relative thereto. In the illustrated embodiment of the invention, four pins 260 are equidistantally spaced relative to each other for positive endwise movement in opposite directions between the retracted and extended positions shown in FIGS. 40 and 42, respectively.

As will be appreciated by those skilled in the art, the exterior configuration of the insert 244 can take a myriad of shapes and forms. According to the present invention, and as illustrated in FIG. 41, the elongated insert 244 preferably has external threading 268 axially extending therealong and leading rearwardly from the first end 246 thereof. The external threading 268 along the exterior of insert 244 has a relatively coarse pitch to enhance the purchasing ability and the anchorage of the anchor 222 within the substance of the bone in response to turning movements being imparted to the anchor 222.

Extending axially forward from the second or trailing end 248, the insert 244 of anchor 222 has a constant generally cylindrical-like configuration 249 extending to the terminal end of the exterior threading 268 and having a slightly smaller outside diameter than that of the exterior threading 268. Notably, the cylindrical-like configuration 249 extending axially forward from the terminal end 248 of the insert 244 has a diameter which is generally equal to the diameter of the throughbore 236 in the guide 220 thereby facilitating sliding movement of the anchor 222 axially within the sleeve 230 of the guide 220. Although not specifically shown, as is conventional, cooperative instrumentalities are defined on the sleeve 230 of guide 220 and on the insert 244. As mentioned above, the purpose of the cooperative instrumentalities is to allow for axial movement of the anchor 222 relative to the sleeve 230 along an axis 252 defined by the insert 244 while preventing rotational movement of the sleeve 230 relative to the anchor 222.

As shown in FIG. 41, insert 244 defines a constant diameter counterbore portion 253 extending axially inward from the first end 246 of insert 244. At an inner end, the counterbore portion 253 defines a radial wall 254. Between end 246 and wall 254, the insert 244 further defines a series of axially elongated openings arranged in spaced circumferential relation relative to each. In the illustrated form of the invention, insert 244 is provided with four openings 270. Each opening 270 intersects with and opens to the counterbore 253 defined by insert 244. As shown in FIG. 41, an axially inward portion 272 of each opening 270 has an inwardly slanted surface for purposes to be described in detail hereinafter.

At an opposite end of the insert 244, another elongated bore 257 having an internally threaded portion 255 and a counterbore portion 256. The internally threaded portion 255 extends inwardly from the second or trailing end 248 of the insert. Preferably, the internally threaded portion 255 of bore 257 has a relatively fine pitched threading extending therealong. Notably, the internally threaded portion 255 has a larger diameter than does counterbore portion 256. The insert 244 further defines a passage 258 extending between counterbore portions 253 and 256.

As shown in FIG. 41, the second or trailing end 248 of the insert 244 is furthermore configured to releasably accommodate a driving tool (not shown) capable of the parting turning movements to the anchor 222. In a preferred form, and as shown in FIG. 41, the trailing or second end of the insert 244 is suitably configured with a slot-like opening 269 for releasably accommodating a distal end of a driving tool. It will be appreciated, however, that any suitable configuration would equally suffice without detracting or departing from the spirit and scope of the present invention.

As shown in FIG. 41, the pins or barbs 260 in this form of the invention form part of a carrier assembly 262. Carrier assembly 262 preferably includes a slide 263 to which one end of each pin 260 is articulately connected to allow the pins 260 to flex or hingedly move relative to the slide while remaining operably connected thereto. As shown, slide 263 has an outer surface configuration 264 having a diameter substantially equal to the diameter of the counterbore portion 253 defined by insert 244. Slide 263 further defines a threaded opening 265 having a relatively fine pitched internal threading extending therealong. Notably, the free ends of the pins 260 are biased to spring outwardly away from the axis 252. Moreover, the free end of each pin 260 has a cam-like surface 266 thereon for purposes to be described in detail hereinafter.

As shown on FIG. 40, the carrier assembly 262 fits axially within bore 253 defined by insert 244 for axial movement and with the pins 260 extending toward the second end 248 of insert 244. After fitting the carrier assembly 262 within bore 253 of insert 244, the open end of insert 244 is closed by an end cap 274.

As shown in FIG. 41 end cap 274 preferably includes a reduced annular portion 275 sized to snugly fit within the free open end of bore 253 defined by insert 244. Suitable retaining means, such as welding, or staking, or the like securely fastens the end cap 274 to the remainder of the insert 244. End cap 274 is preferably formed from a material that is biocompatible with bone tissue or human substance and is preferably selected from the class comprised of: titanium or titanium alloy, stainless steel, or cobalt chromium alloy. It would be appreciated, however, that other unnamed materials would equally suffice without detracting or departing from the spirit or scope of the present invention.

As shown in FIG. 41, the end cap 274 defines a central throughbore or hole 276 extending therethrough. Moreover, the annular or circumferential surface of end cap 274 is preferably chamfered to promote insertion of the anchor 222 into the bone.

Returning to FIG. 40, when the carrier assembly 262 is mounted within bore 253 of insert 244, the pins 260 tend to bias outwardly. The slots or opening 270 in the insert 253 are elongated such that a distal end of each pin 260 tends to project radially outwardly into the slot 270 with the slanted surface 266 being advantageously arranged to engage and cooperate with slanting surface 272 on each opening 270 in a manner forcibly projecting the pins 260 radially outwardly as shown in FIG. 42.

The mechanism 280 for positively displacing the pins 260 in opposite directions between retracted and extended positions (FIGS. 40 and 42, respectively) will now be described. The drive mechanism 280 preferably includes a manually operated driver 282 arranged in operative relation with the carrier assembly 262. As will be described below, manual activation of the drive mechanism 280 will affect axial displacement of the carrier assembly 262 within bore 253 of insert 244 thereby effecting positive displacement of the pins 260 with the carrier assembly 262.

Turning to FIG. 41, driver 282 preferably includes an axially elongated and hollow member 284 having a reduced diameter portion 286 axially projecting rearwardly from a first end 288 thereof. The driver 282 is formed from a material that is bio-compatible with bone tissue or human substance and is preferably selected from the class comprised of: titanium, titanium alloy, stainless steel, or cobalt chromium alloy. Of course, other unnamed materials will equally suffice without detracting or departing from the spirit and scope of the present invention. The reduced diameter portion 286 of member 284 has a diameter equal to the diameter of bore 276 defined by end cap 274. At a second end 290, driver 282 has an enlarged head portion 292. In a preferred form, and as shown in FIG. 41, the second end 290 is configured to releasably to accommodate a distal end of a driving tool. In a most preferred form of the invention, the second or terminal end 290 of driver 282 is provided with an elongated slot 294 that is configured to releasably accommodate a driving tool. Axially spaced inwardly from the terminal end 290 thereof, the driver 282 is provided with an axially extended shoulder 295. Between the shoulder and the reduced diameter portion 286, the driver 282 is provided with external threading 296. The external threading extending lengthwise along the driver 282 has a relatively fine pitch that corresponds to the internally threaded portion 265 of slide 263 forming part of the carrier assembly 262. Notably, the reduced diameter portion 286 and the externally threaded portion 296 of driver 282 are sized to permit their endwise insertion through passage 258 defined by insert 244. Moreover, the shoulder portion 295 has a diameter that is substantially equal to the passage 258 and is journalled thereby. Moreover, the enlarged head portion 292 is specifically sized with the diameter greater than the passage 258 thereby preventing axial displacement or movement of the head portion 292 past the passage 258.

During assembly of the surgical fastener assembly 210, the reduced diameter portion 286 and externally threaded portion 296 are passed endwise through the passage 258 defined in the insert 244 of anchor 222. The threaded portion 296 of driver 282 is likewise threadably engaged with the slide 263 of carrier assembly 262 to allow the reduced diameter portion 286 to pass endwise through and be journalled by the periphery of the bore 276 defined by end cap 274. The reduced diameter portion 286 is sized to allow a lengthwise portion thereof to pass endwise through and beyond the end cap 274. That free end of the reduced diameter portion 286 is thereafter swaged or flared outwardly thus preventing axial displacement of the driver 282 in response to rotational movement being imparted thereto.

Turning to FIG. 42, the pins 260 of carrier assembly 262 are radially and positively displaced in opposite directions relatively to axis 252 in response to and as a function of rotation of driver 282. As shown, a suitable tool 297 is displaced endwise through bore 236 of guide 220 and through the bore 257 of insert 244 into operable engagement with the slot 294 at the second end 290 of driver 282. Thereafter, rotation of the driver 282 will result in axial or endwise displacement of the slide 263 as a result of the threaded interconnection between the internal threading 265 on slide 263 and the external threading 296 on driver 282. As will be appreciated, and as the pins 260 are drawn toward the radial wall 254 of bore 253, the slanted surface configurations 266 thereon engage the outwardly slanting surfaces 272 of the openings thereby forcibly propelling the pins radially outwardly relative to the axis 252. As will be appreciated, rotation of the tool 297 in the opposite direction will likewise result in axial displacement of the carrier assembly 262 but in a direction opposed from that earlier discussed. As a result, the turning or rotation of the driver 282 will affect retraction of the pins 260 as the slide assembly 262 is moved in a direction toward the end cap 274.

Another aspect of the present invention relates to the surgical anchor assembly 210 having a compressive screw assembly 224 for maintaining the guide 220 and anchor 222 in compressive relationship relative to each other as by axially fixing the guide 220 to the anchor 222. In that embodiment shown in FIG. 41, the compression screw assembly 224 preferably includes a compression screw 300 and a driver 302. Both the compression screw 300 and driver 302 are formed from a material that is bio-compatible with bone tissue or human substance material and is preferably selected from the class comprised of titanium, a titanium alloy, stainless steel, or cobalt chromium alloy.

As shown in FIG. 41, the compression screw 300 is provided with first and second interconnected sections 304 and 306. The sections 304 and 306 of compression screw 300 are joined or interconnected to each other by a collapsible section 308 that transmits rotation and torque between the sections 304 and 306. The first section 304 of compression screw 300 is provided with an elongated shank portion 312 and an enlarged head portion 314. The shank portion 312 of the first section 304 is provided with external threading 316 therealong. The external threading 316 has a relatively fine pitch that corresponds to the internal threading 255 extending along the bore 257 of insert 244. As shown in FIG. 43, the enlarged head portion 314 of the first section 304 of screw 300 has a diameter slightly smaller than the diameter of the counterbore 238 defined by guide 220. Notably, the head portion 314 of screw 300 is preferably configured to releasably accommodate a driving tool capable of imparting turning movements to the screw section 304.

In a preferred form, and as shown in FIG. 41, the trailing end of screw section 304 is configured with a slot 318 for releasably accommodating a distal end of a driving tool. Notably, the first section 304 of screw 300 is fixed to the collapsible section 308 such that turning movements imparted to screw section 304 will likewise be imparted to the collapsible section 308.

The second screw section 306 is likewise connected to the collapsible section 308 in axially spaced relation relative to screw section 304. As shown, screw section 306 includes external threading 326 extending along the length thereof. Notably, the external threading 326 on screw section 306 is identical to the external threading 316 on screw section 304.

The collapsible section 308 serves to transfer the motion of screw section 304 to screw section 306. Moreover, the second screw section 306 defines an internally threaded portion 330 extending therealong. The threaded portion 330 of the second screw section 306 has a relatively fine pitched threading extending therealong. Notably, however, the threading extending along portion 330 is left-handed threading while the external threading 316 and 326 on screw portions 304 and 306, respectively, is right handed. As will be appreciated, the threading along screw portion 330 and 316, 326 can be right handed and left handed, respectively, without detracting or departing from the spirit and scope of the present invention. The important aspect to note is that the threading along portions 330 and 316, 326 are reversed from each other.

As shown in FIG. 41, the driver 302 of compression screw assembly 224 comprises a shank portion 334 and an enlarged head portion 336. The shank portion 334 of driver 302 has a diameter sized to allow the shank portion 334 to slidably to fit endwise into and through the central interior of screw 300. The shank portion 334 of driver 302 includes external threading 340 axially extending from a free end 342 of the driver 302. The head portion 336 of driver 302 is sized to prevent it from passing through the interior of screw 300. As will be appreciated, the axial length or distance separating head portion 336 of screw 302 from the free end 342 thereof is about equal to the distance separating the head portion 314 of screw 300 from the beginning portion of the interior threading 330 most closely adjacent the head portion 314.

In a preferred form, and as shown in FIG. 41, the trailing end of the head section 336 of driver 302 is configured with a slot 344 for releasably accommodating the distal end of a driving tool. As will be appreciated, configurations other than a slot would equally suffice without detracting or departing from the spirit and scope of the present invention.

During assembly of the surgical fastener assembly 210, and as shown in FIG. 43, the compressive screw 300 of the compressive screw assembly 224 is rotatably threaded into engagement with the internal threading 255 of the insert 244. A suitably configured tool 355 engages with the slot 318 and the head portion 314 of the screw 300 to drivingly rotate the first and second sections 304 and 306 of the screw 300 until the enlarged head 314 abuts the radial wall 240 defined by the counterbore 238 defined by the guide 220. Thereafter, the driver 302 is operably engaged with the screw 300. That is, and is shown in FIG. 44, the driver 302 is inserted through the central opening defined by the screw 300 into threaded engagement with the internal threading 330 of the second section 306 of screw 300. Notably, however, the driver 302 is turned in a direction opposed from that in which the screw 300 was rotated for insertion into the anchor. In this regard, a suitable tool 357 releasably engages with the slot 344 in the head region 336 of the driver 302 to rotate the driver 302. Rotation of the driver 302 is affected until the section 308 joining sections 304 and 306 collapses. The collapse of the center section 308 causes opposing forces to act against the external threading on sections 304, 306 and the internal threading 330 thereby preventing the compressive screw assembly 224 from inadvertently turning relative to the anchor 222.

FIG. 45 schematically illustrates an alternative form of anchor, generally represented by reference to numeral 422 that can be used as part of the surgical anchor assembly. The anchor 422 includes an elongated insert 444 having opposed first and second ends 446 and 448. The insert 444 is preferably formed from a material similar to that used to form insert 44. Insert 444 is sized such that when inserted within the bone, the first end 446 is disposed to one side of a fracture line while the second end 448 of the insert 444 is disposed to an opposite side of the fracture line.

Figure 63:
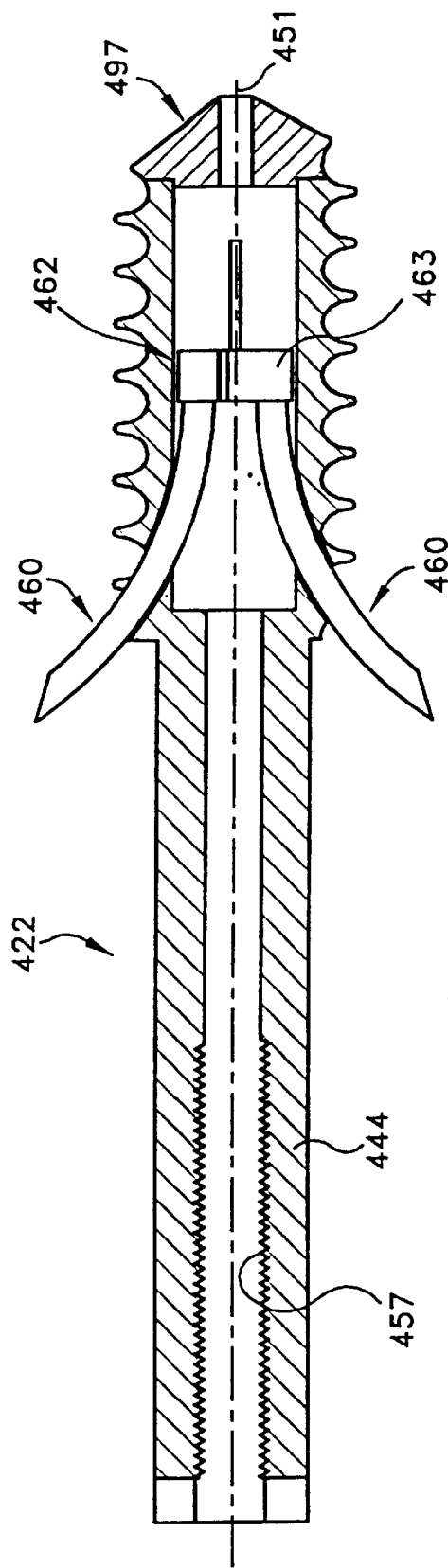
FIG. 63 is a longitudinal sectional view similar to FIG. 45 but showing the pins arranged in an extended relationship relative to the anchor.

As shown in FIGS. 45 and 46, the anchor 422 of the surgical fastener assembly further includes a series of elongated pins or barbs 460 operably associated toward the first end 446 of the insert 444. As shown in FIGS. 45 and 63, the pins or barbs 460 are operably associated with the anchor 422 for movement between a retracted position (FIG. 45) and a radially extended position (FIG. 63). As shown, the pins 460 are carried by the insert 444 for endwise and radial displacement relative thereto. In the illustrated embodiment of the invention, two pins 460 are carried by the anchor 422 in diametrically opposed relation relative to each other for positive endwise movement in opposite directions between the retracted and extended positions shown in FIGS. 45 and 63, respectively.

According to this aspect of the present invention, and as illustrated in FIGS. 46 and 47, the elongated insert 444 preferably has external threading 468 axially extending there along and leading rearwardly from the first end 446 thereof. The external threading 468 along the exterior of insert 444 has a relative coarse pitch to enhance the purchasing ability and the anchorage of the anchor 422 within the substance of the bone in response to turning movements being imparted to the anchor 422.

Extending axially forward from the second or trailing end 448, the insert 444 of anchor 422 has a constant generally cylindrical-like configuration 449 extending to the terminal end of the exterior threading 468 and having a slightly smaller outside diameter then that of the exterior threading 468. Notably, the cylindrical-like configuration 449 extending axially forward from the terminal end 448 of the insert 444 has a diameter which is generally equal to the diameter of the throughbore 36 (FIG. 2) in the guide operably associated therewith thereby facilitating sliding movement of the anchor 422 axially within the sleeve of the guide. Although not specifically shown, and as is conventional, cooperative instrumentalities are defined on the exterior configuration 449 of the insert 444 and of the respective guide to allow for axial movement of the anchor 422 relative to the guide along an axis 451 defined by the insert 444 while preventing rotational movement of the anchor 422 relative to the respective guide.

As shown in FIG. 47, insert 444 defines a constant diameter counterbore portion 452 extending axially inward from the first end 446 of insert 444. At an inner end, the counterbore portion 452 defines a radial wall 454. Between end 446 and wall 454, the insert further defines a pair of slanted openings 470 arranged in diametrically opposed relation relative to each other. Each opening intersects with and opens to the counterbore 452 defined by insert 444. Moreover, each opening 470 opens to the exterior of insert 444.

Extending axially forwardly from the second or opposed end 448, the insert 444 defines an elongated bore 455 that opens to the counterbore portion 452. Extending inwardly from the second end 448, bore 455 includes an internally threaded portion 457. Preferably, the internally threaded portion 457 of bore 455 has a relatively fine pitched threading extending therealong. As should be appreciated, the internal threading 457 corresponds to the external threading on the compressive screw assembly (not shown) arranged in operable combination with the insert 444.

As shown in FIG. 47, the second or trailing end 448 of insert 444 is furthermore configured to releasably accommodate a driving tool (not shown) capable of imparting turning movements to the anchor 422. In a preferred form, and as shown, the trailing or second end 448 of the insert 444 is suitably configured with a slot-like opening 469 for releasably accommodating a distal end of a driving tool. It will be appreciated, however, that any suitable configuration would equally suffice without detracting or departing from the spirit and scope of the present invention.

Turning to FIG. 49, the insert 444 is further provided with a suitable guide mechanism 475 for purposes to be described hereinafter. The guide mechanism 475 can take a myriad of different forms without detracting or departing from the spirit and scope of the present invention. One form of guide mechanism 475 is schematically illustrated in FIG. 49. In the illustrated embodiment, the guide mechanism 475 includes a pair of diametrically opposed guide keys 477 and 479 that extend along a lengthwise portion of the counterbore 452 defined by insert 444. As shown in FIG. 49, the guide keys 477 and 479 project radially inwardly toward each other. Notably, the distal end of each guide key 477 and 479 terminates short of the first end 446 of the fastener 444 such that there is an axial space between the terminal end of the guide of each guide key 477, 479 and the first end 446 of the insert 444.

Returning to FIG. 45, the pins or barbs 460 in this form of the present invention form part of a carrier assembly 462. Carrier assembly 462 preferably includes a slide 463 to which one end of each pin is fixedly connected such that the pins 460 will positively move upon axial movement of the slide 463 within the counterbore 452 of insert 444.

Turning to FIGS. 46, 50 and 51, each pin 460 has a flexible wire-like configuration shaped to slidably fit endwise within and through a respective one of the openings 470 defined in the insert 444. Suffice it to say, each pin 460 is provided with sufficient strength so as to allow for insertion in and through the bone tissue without substantially bending intermediate opposite ends thereof. In a most preferred form of the invention, each pin 460 is formed from a material selected from the class comprised of: titanium, a titanium alloy, stainless steel, or cobalt chromium alloy.

In the embodiment illustrated in FIGS. 46, 50 and 51, each pin 460 has a leading end 461 in an opposite pointed end 466. Toward end 466, each pin preferably has a curvilinear or arcuate configuration such that the free ends 466 extend into and through the opening 470. The length of each pin 460 is selected such that when the leading end 461 of the pin 460 is fully retracted within the anchor 422 (FIG. 45) the opposite pointed end 466 of the pin or barb 460 will be positioned within the outside diameter of the insert 444 to facilitate insertion of the surgical anchor assembly within the bone of the patient. Moreover, it is to be appreciated that the length of each barb or pin 460 is sized such that when the pins are displaced to their extended position (FIG. 63) the leading end 461 of each pin 460 remains operably associated with the carrier assembly 462 to allow for positive retraction of the pins 460 from their extended positions when desired or found necessary by the surgeon.

As mentioned, the slide assembly 462 further includes a carrier 463. The configuration of the slide 463 is illustrated in FIGS. 52 through 55. As shown, slide 463 has a generally cylindrical outer surface configuration having a diameter substantially equal to the diameter of the counterbore portion 452 (FIG. 46) of fastener 444. Slide 463 defines an identical pair of throughbores or openings disposed in diametrically opposed relation relative to each other. The diameter of the openings 481, 483 are sized to receive the end 461 of pin 460 and to allow the ends 461 of each pin 460 to be rigidly secured thereto. Additionally, the slide 463 defines a pair of diametrically opposed slots 485 and 487 that are arranged in other than a normal relation relative to the openings 481 and 483. Notably, the slots 485, 487 are sized to facilitate guided movement of the slide 463 relative to the guide keys 477 and 479 on the insert 444 (FIG. 62). Moreover, the slide 463 defines a tool engagement cavity 491 that passes endwise through the slide and has recesses 493 and 495 on opposite sides thereof.

As shown in FIG. 45, the carrier assembly 462 fits axially within the bore 452 defined by insert 444 for axial movement and with the pointed ends 466 of each pin 460 extending at least partially through the opening 470, but not beyond the periphery of fastener 444. After fitting the carrier assembly 462 within the bore 452 of insert 444, the open end of insert 444 is closed by an end cap 497.

Figure 58:
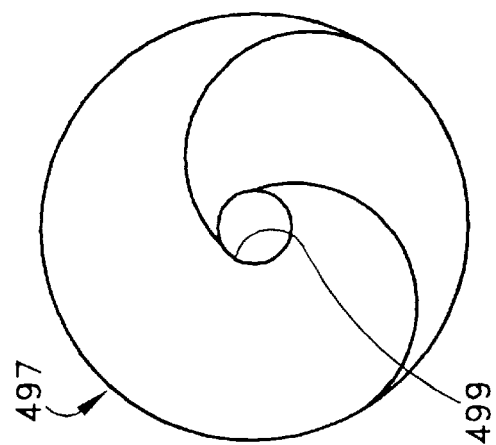
FIG. 58 is a right end view of the end cap shown in FIG. 56.
Figure 56:
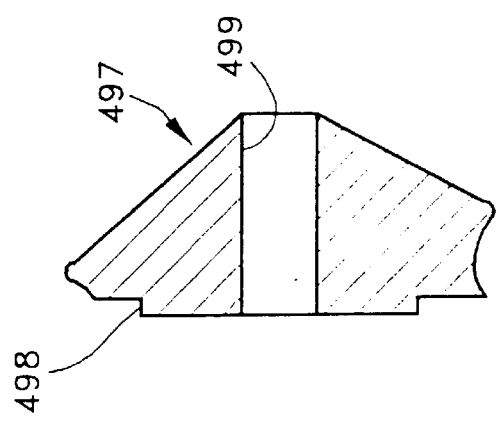
FIG. 56 is a sectional view of an end cap forming part of the third embodiment of the present invention.
Figure 57:
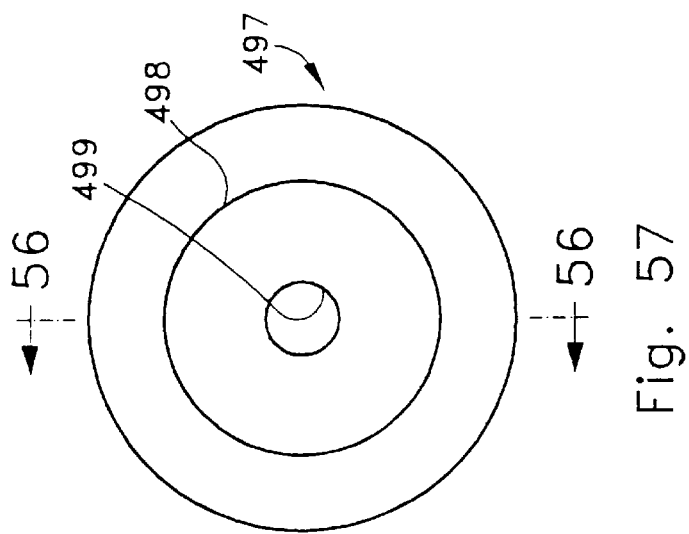
FIG. 57 is a left end view of the end cap shown in FIG. 56.

A preferred form of end cap 497 is illustrated in FIGS. 56, 57 and 58. As shown, end cap 497 preferably includes a reduced annular portion 498 sized to snugly fit within the free open end of bore 452 defined by insert 444. Suitable retaining means such as staking, welding or the like securely fastens the end cap 497 to the remainder of the insert 444. End cap 497 is preferably formed from material that is biocompatible with bone tissue or a human substance and is preferably selected from the class comprised of: titanium, a titanium alloy, stainless steel, or cobalt chromium alloy. Other unnamed materials would equally suffice, however, without detracting or departing from the spirit or scope of the present invention. As shown in FIGS. 56 through 58, the end cap 497 defines a central throughbore or hole 499. Moreover, the exposed surface of end cap 497 is preferably chamfered to promote insertion of the anchor 422 into the bone.

Figure 60:
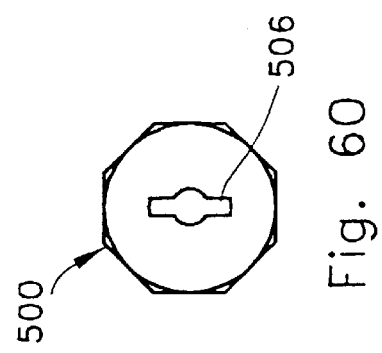
FIG. 60 is a right end view of the tool shown in FIG. 59.
Figure 59:
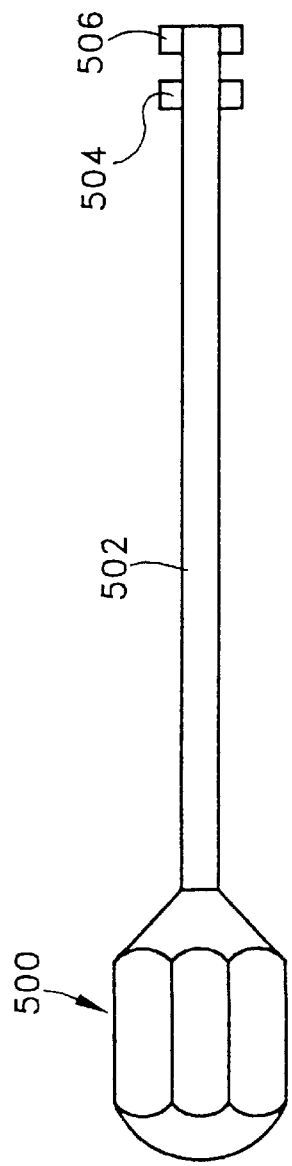
FIG. 59 is a side elevational view of a tool used to extend and retract the pins in the third embodiment of the anchor assembly shown in FIG. 45.

FIGS. 59 and 60 schematically illustrate a tool that is configured to cooperate with and axially move the carrier assembly 462 in opposite directions within the bore 452 of the insert 444 whereby positively moving the pins 460 between retracted (FIG. 45) and extended (FIG. 63) positions. The tool 500 preferably includes an elongated shank 502 having axially spaced keys 504 and 506 at a distal end thereof. The shank 502 and keys 504 and 506 are configured to axially fit endwise within the bore 455 of insert 444 and extend into operable combination within the slide 463 of the carrier assembly 462. More specifically, the key 506 is specifically configured to fit endwise through the tool engagement cavity 491 such that the key 506 can operably engage with the surfaces 493 and 495 on the slide.

As shown in FIG. 45, the guide slots 485 and 487 in the slide 463 are not axially aligned with the guide keys 477 and 479 extending radially inwardly from the bore 452. As will be appreciated by those skilled in the art, the guide keys 477 and 479 are radially offset from the guide slots 485 and 487, respectively, under the influence of the disposition of the pins 460 and their orientation relative to the guide slots 485 and 487. Accordingly, the slide assembly 462 cannot be inadvertently displaced axially within the bore 452 and the pins 460 remain in the retracted positions.

Figure 62A:
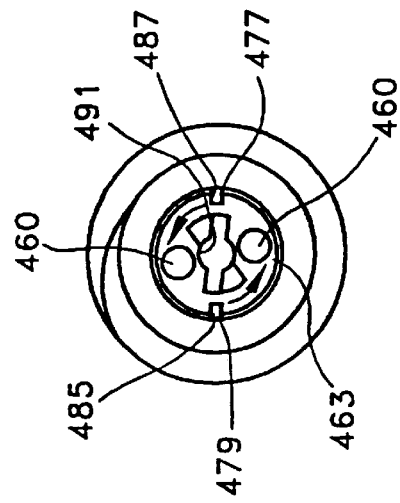
FIG. 62A is a sectional view taken along line 62A—62A of FIG. 62.
Figure 61A:
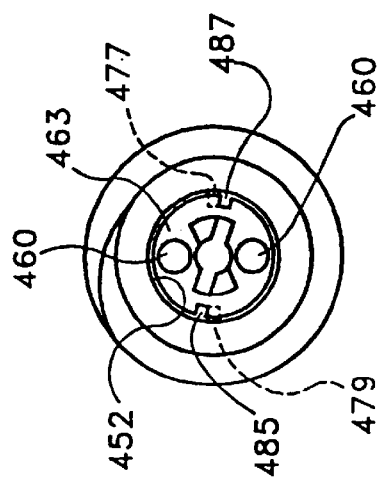
FIG. 61A is a sectional view taken along line 61A—61A of FIG. 45.

To affect extension of the pins or barbs 460 radially outwardly from the bore 452 of the fastener 444, the tool 500 is inserted through the fastener 444. More specifically, the keys are endwise inserted through the insert 444 and allow to pass into operable engagement with the slide. After moving the keys 504 and 506 into operable engagement with the slide, the tool 500 is rotated to effect rotation of the slide 463 as shown in arrows and FIGS. 62 and 62A. Rotation of the slide 463 is permitted by the resiliency of the length of the pins 460. The slide 463 is rotated until the slots 485 and 487 are aligned with the guide keys 477 and 479 and thereafter the tool 500 is moved to the left as shown in FIG. 62 to forcibly propel the pins 460 outwardly relatively to the insert 444 thereby enhancing securement of the surgical anchor 422 into the bone. When desired, the tool may also be used in operable engagement with the slide 462 to forcibly retract the pins 460 to the position shown in FIG. 45. That is, the keys are rearranged in operable engagement with the slide 463 and the tool 500 is pushed and turned or rotated to forcibly retract the pins to facilitate removal of the anchor assembly when necessary or desired by the surgeon.

Still another alternative form of compression screw assembly, generally represented by reference numeral 600, is illustrated in FIGS. 64 and 64A. The purpose of the compression screw assembly 600 is to maintain a guide 620 and anchor 622 in compressive relationship relative to each other as by fixing the guide 620 to the anchor 622. For purposes of this description, the guide 620 and anchor 622 are substantially similar to the guide 20 and anchor 22 described above. Thus, no further detailed description need be provided therefore at this time.

The compressive screw assembly 600 preferably includes a compression screw 630 and a driver 650. Both the compression screw 630 and driver 650 are formed from a material that is biocompatible with bone tissue or human substance.

As shown in FIG. 65, the compression screw 630 is provided with an elongated shank portion 632 and an enlarged head portion 633. The shank portion 632 of the compression screw 630 is provided with external threading 634 extending axially from a leading end 635 of the screw 630. The external threading 634 has a relatively fine pitch that corresponds to internal threading extending axially along an internally threaded bore 678 of anchor 622. The enlarged head portion 633 of screw 630 has a diameter slightly smaller than the diameter of a counterbore 688 formed in guide 620 and which is substantially similar to counterbore 38 in guide 20 (FIG. 2).

As shown in FIG. 65 and 66, a trailing end 636 of screw 630 is preferably configured to releasably to accommodate a driving tool (not shown) capable of imparting turning movements to the screw 630. In a preferred form, and as shown, the trailing end 636 of screw 630 is configured with a socket-like opening 637 having a bottom 638. The socket-like opening 637 is configured to releasably accommodate a distal end of a driving tool. In a most preferred form of the invention, and as shown, the socket or opening 637 has a hexagonal-like cross-sectional configuration. It will be appreciated, however, that any suitable configuration including an elongated slot would equally suffice without detracting or departing from the spirit and scope of the present invention.

The screw 630 furthermore defines an elongated bore 640 that opens at opposite ends to the socket 637 and the leading end 635 of screw 630. As shown, the opening 640 has internal treading 642 extending along the length thereof. As shown in FIG. 65 and 67, the distal or leading end 635 of the screw 630 is provided with a series of radial through slots 643, 644, 645, and 646 that are arranged in generally normal relation relative to each other and which extend axially inwardly from the fray or distal end 635 for a predetermined distance.

Moreover, and as shown in FIG. 65, the internal bore 640 and the internal threading 642 narrow toward the fray or distal end of the 635 of screw 630 in the area of the slots 643, 644, 645 and 646 for purposes to be described hereinafter.

As mentioned above, the compression screw assembly 600 further includes a driver 650 to be arranged in combination with the screw 630. The driver 650 is illustrated in FIGS. 68, 69 and 70. Driver 650 includes a shank portion 652 and a enlarged headed portion 654. The shank portion 652 of driver 650 is provided with external threading 656 extending axially from a leading end 658 of the driver 650. The external threading 656 has a relatively fine pitch that corresponds to the internal threading 642 provided bore 640 of screw 630. The enlarged head portion 654 of driver 650 has a diameter slightly smaller than that which can be endwise accommodated within the socket 637 of screw 630. As will be appreciated from an understanding of the compression screw assembly 630, the length of the shank portion 652 is sufficient such that the distal or free end 658 operably extends to and through the slotted end of screw 630 when the head portion 654 bottoms at the floor 638 of socket 637.

As will be appreciated from an understanding of the compression screw assembly 600, the compression screw 630 is threaded into the anchor assembly 622 as shown in FIG. 64, to draw the guide 620 into compressive relationship relative to the anchor 622. Thereafter, the driver 650 is threaded into engagement with the internal threading 642 of screw 630. Notably, the outside diameter of the shank portion 632 of screw 630 is substantially constant as long as the driver 650 remains out of engagement with the slotted end 635 of screw 630. Once the appropriate compression has been achieved between guide 620 and anchor 622, the driver 650 is further engaged with the compression screw as shown in FIG. 73. As a result, the slotted end 635 of screw 630 is expanded radially outwardly thus providing for a compressive fit which prevents the compression screw assembly 600 from rotating relative to the anchor 622 and thereby maintaining the compressive relationship between the guide 620 and anchor 622.

Figure 74:
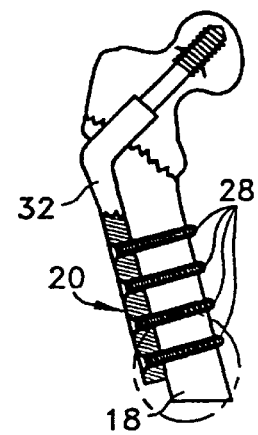
FIG. 74 is a reduced view similar to FIG. 2.

As mentioned above, and as schematically represented in FIG. 74, a series of screws 28 are used to fasten plate 32 of guide 20 to bone fragment 18. Another aspect of the present invention relates to a preferred form of construction for the screw 28 used to fasten the plate 32 of guide 20 to the bone fragment 18.

Figure 75:
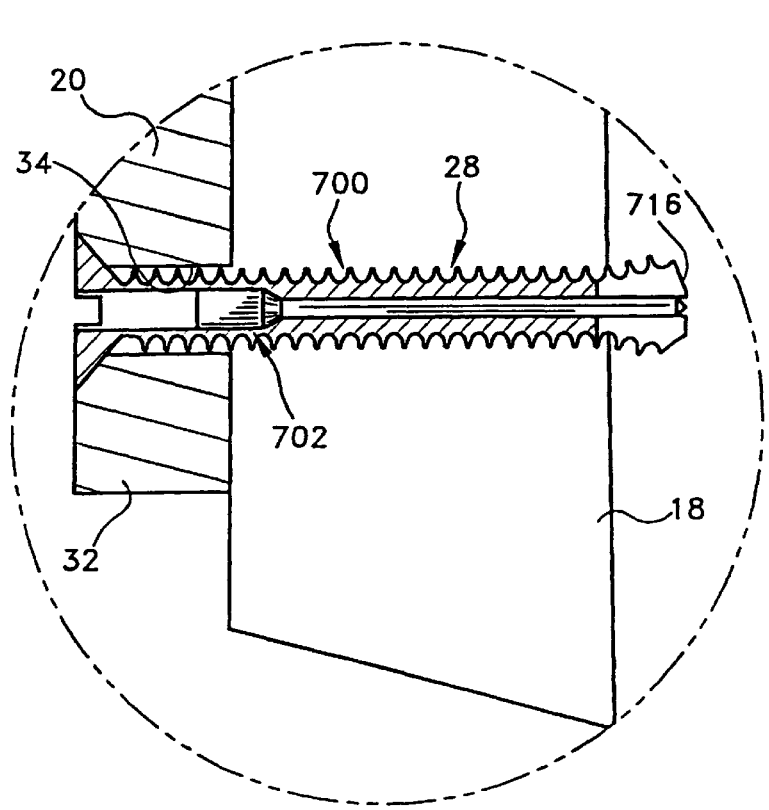
FIG. 75 is an enlarged view of that area encircled in FIG. 74.

In the preferred embodiment, and as shown in FIG. 75, screw 28 comprises an elongated cannulated fastener 700 and a driver 702. As will be appreciated, fastener 700 is formed from a material that is biocompatible with bone tissue and includes a shank portion 710 and an enlarged head portion 712. The shank portion 710 of fastener 700 is provided with external threading 714 extending axially from a leading end 716 of the fastener 700. The external threading 714 has a pitch that promotes purchase and securement of the fastener 700 within the bone substance. The enlarged head portion 712 of fastener 700 is configured to cooperate with the shape of the throughhole 34 in the plate 32 of guide 20. In the illustrated embodiment, the head portion 712 of fastener 700 has a frusto-conical like configuration that cooperates with a countersunk configuration or recess in the throughhole 34 to secure the plate 32 to the bone 18. It will be appreciated, however, that shapes other than that shown for the head portion 712 and throughhole 34 would equally suffice without detracting or departing from the spirit and scope of the disclosure.

Figure 76:
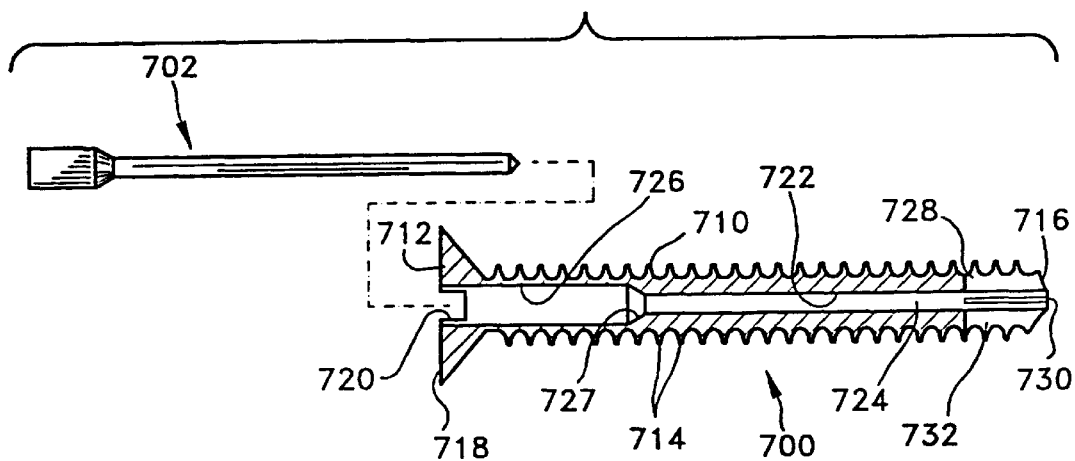
FIG. 76 illustrates component parts of an alternative form of a screw assembly used to secure the guide to the bone, with the component parts thereof shown in disassembled relationship relative to each other.

As shown in FIG. 76, a trailing end 718 of fastener 700 is preferably configured to releasably to accommodate a driving tool (not shown) capable of imparting turning movements to the fastener 700. In a preferred form, and as shown, the trailing end 718 of fastener 700 is configured with an elongated slot or opening 720. The slot 720 is configured to releasably accommodate a distal end of a driving tool. As will be appreciated, however, any suitable configuration including a socket would equally suffice for releasably accommodating a distal end of a driving tool without detracting or departing from the spirit and scope of the present invention.

The cannulated fastener 700 furthermore defines an elongated bore 722 that opens at opposite ends 716, 718 of fastener 700. As shown in FIGS. 76 and 77, the bore or opening 722 has a first section 724 opening to the first end 716 of fastener 700 and having a first diameter and a second counterbore portion 726 opening to the trailing or second end 718 of fastener 700 and having a second diameter. Notably, the diameter of bore 726 is larger than the diameter of bore or opening 722 and, thus, a radial wall or annular shoulder 727 is defined by the differences in diameters therebetween. As shown in FIGS. 77 and 79, the distal or leading end 716 of the fastener 700 is provided with a series of radial through slots 728, 730, 732 and 734 that are arranged in generally normal relation relative to each other and which extend axially inwardly from the first or distal end 716 of fastener 700 for a predetermined distance. As shown, and for purposes described hereinafter, the diameter of the first portion 724 of bore 722 narrows or is reduced in the area of the slots 728 through 734 while the outside diameter of the fastener remains substantially constant.

As will be appreciated from an understanding of this embodiment, the axial length of the shank portion 710 of fastener 700 is such that when the fastener is passed through the throughhole 34 in the plate 32 of guide 20 and secured within the bone 18, the axial lengthwise portion of the shank 710 with the slots formed therein will extend beyond the bone 18 by a distance equal to about the length of the slots 728 through 734. Of course, during surgery, a surgeon may have a collection of different fasteners to choose from; with each fastener having a different length such that a proper relationship of the fastener to bone thickness is readily obtainable for the surgeon.

As mentioned above, this form of screw 28 further includes a driver 702 arranged in combination with fastener 700. A preferred from of driver 702 is illustrated in FIGS. 80 through 82. As shown, driver 702 preferably includes a one-piece member 750 formed from a material that is biocompatible with human bone tissue and substance. Driver member 750 includes a first section 752 with a substantially constant diameter along its length and an axially aligned second section 754 having a substantially constant diameter along its length. The second section 754 has a larger diameter than the first section 752 and, thus, a radial wall or annular shoulder 757 is defined therebetween.

In the illustrated embodiment, the annular shoulder or annular wall 757 on the driver 702 generally corresponds to the radial wall or annular shoulder 727 defined by fastener 700. It is important to note, however, the axial length of the first section 752 extending between the radial wall or annular shoulder 757 and the free end of driver member 750 is generally equal to the distance separating the radial wall or annular shoulder 727 from the distal or free end 716 of fastener 700. Moreover, the first section 752 of driver 702 is sized to establish a sliding fit within the first section 724 of bore 722 defined by fastener 700. In a most preferred form of the invention, the second section 754 of driver 702 is sized to establish a sliding fit within the second section 726 of bore 722 defined by fastener 700.

Figure 83:
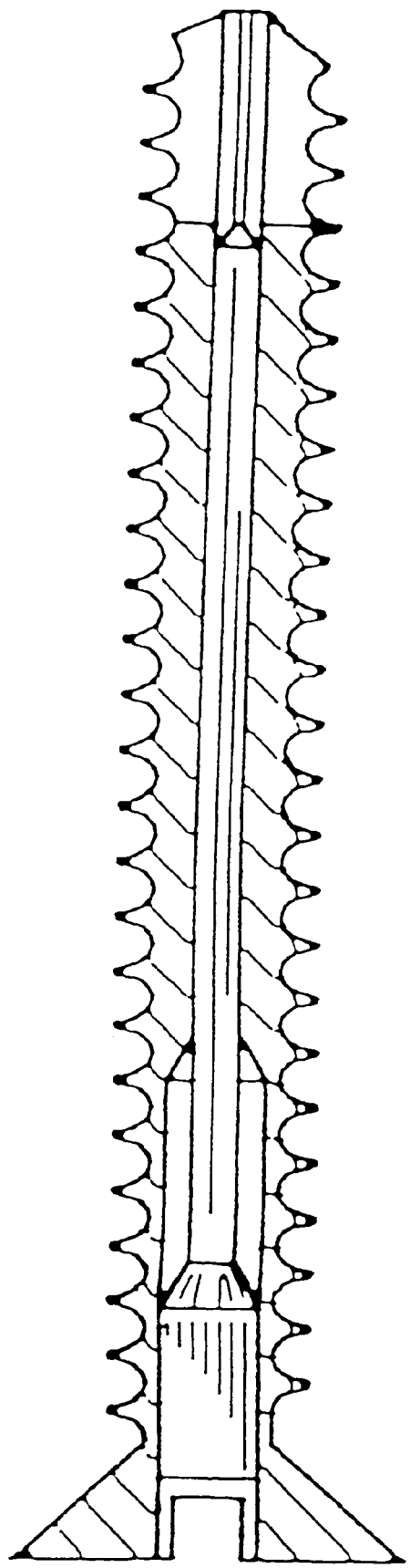
FIG. 83 is a view showing the driver partially arranged in operable association with the compression screw.

As will be appreciated from an understanding of the screw 28, and as shown in FIG. 75, the first or forward end 716 of the fastener 700 is passed endwise through the throughbore 34 in plate 32 of guide 20 and the shank portion 710 is threaded into the bone 18 by turning the head portion 712. Ultimately, the head portion 712 will contact the plate 32 and draw the guide 620 into a secured relationship relative to the bone. At this point, the slotted free end of the fastener 700 will extend beyond the bone 18 on that side thereof opposite from the plate 32 of guide 20. Notably, as the fastener 700 is secured within the bone 18, the outside diameter of the shank portion 710 of screw 700 is substantially constant as long as the driver 702 remains out of engagement with the fastener 700. Once the appropriate securement has been achieved between guide 620 and cannulated fastener 700, the driver 702 is driven through the bore 722 of fastener 700 as shown in FIG. 83. When the driver 702 is fully inserted into the fastener 700, as when the shoulder 757 on the driver member 750 engages with the shoulder 727 on the fastener 700, the slotted end 716 of fastener 700 is expanded radially outwardly thus preventing inadvertent rotation of the fastener 700 thereby maintaining the secured relationship between the guide 20 and bone 18 as shown in FIG. 75.

From the foregoing, it will be observed that numerous modifications and variations can be effected without departing from the true spirit and scope of the novel concept of the present invention. It will be appreciated that the present disclosure is intended to set forth exemplifications of the invention, and the exemplifications set forth are not intended to limit the invention to the specific embodiments illustrated. The disclosure is intended to cover by the appended claims all such modifications as fall within the spirit and scope of the claims.

What is claimed is:

1. A surgical fastener assembly for coupling first and second bone portions across a fracture therebetween, said fastener assembly comprising:

an elongated anchor endwise insertable within the first bone portion such that a first end portion of said anchor is disposed on one side of the fracture while a second end portion of the anchor is disposed on an opposite side of the fracture, wherein a threaded elongated bore extends within said anchor;

a guide adapted to be fixedly secured to the second bone portion, with a projection on said guide being guided by and along the second end portion of said anchor;

a cannulated fastener including an enlarged head portion and an externally threaded shank portion with an elongated bore extending through said head and shank portions and opening at opposite ends of said fastener, wherein, in an operative position, the shank portion of said fastener extends into threaded engagement with said anchor while the head portion of said fastener operably engages with said guide such that rotation of said fastener draws the first and second bone portions into compressive relationship relative to each other; and a retainer positioned within said bore extending within said anchor, the retainer being threadably associated with the second end of said anchor and positionable relative to said fastener for releasably locking said fastener to prevent axial displacement of said guide in a direction away from said anchor.

2. The surgical fastener assembly according to claim 1 wherein said retainer is engagable by a tool extendable through the bore of said fastener to position said retainer relative to said fastener.

3. The surgical fastener assembly according to claim 1 wherein said anchor is formed from a material chosen from a class comprised of: titanium, a titanium alloy, stainless steel, or a cobalt chromium alloy.

4. The surgical fastener assembly according to claim 1 wherein said guide is formed from a material chosen from a class comprised of: titanium, a titanium alloy, stainless steel, or a cobalt chromium alloy.

5. The surgical fastener assembly according to claim 1 wherein said retainer defines an axial bore configured to operably engage with a tool whereby turning movement can be imparted to said retainer.

6. The surgical fastener assembly according to claim 1 wherein said anchor has external threading extending over and along an axial length thereof for fastening said anchor within the first bone portion.

7. The surgical fastener assembly according to claim 6 wherein the second end of said anchor is configured to releasably accommodate a driving tool capable of imparting turning movements to said anchor such that the external threading thereon engages the bone substance of the first bone portion.

8. The surgical fastener assembly according to claim 1 wherein said guide defines a recess sized to accommodate the head portion of said fastener therewithin and such that no portion of said fastener extends axially beyond said guide after said guide is fastened to said anchor.

9. The surgical fastener assembly according to claim 1 wherein said guide and said anchor are releasably fastened to each other to prevent relative rotation therebetween.

10. A surgical fastener assembly for coupling first and second bone portions across a fracture therebetween, said fastener assembly comprising:

an elongated anchor endwise insertable within the first bone portion such that a first end region of said anchor is disposed on one side of the fracture while a second end region of the anchor is disposed on an opposite side of the fracture and wherein said anchor includes external threading extending along a lengthwise portion thereof for effecting securement of said anchor within the first bone portion;

a series of pins operably associated with said first end of said anchor for movement between extended and retracted positions, wherein when pins are in said retracted position they have no operable anchoring effect between said anchor and the first bone portion, and wherein when said pins are in said extended position they radially extend outwardly from said anchor while remaining in operable association therewith thereby securing said anchor within the first bone portion;

a mechanism for positively moving said pins in opposite directions between said extended and retracted positions;

a guide adapted to be fixedly secured to the second bone portion, with a projection on said guide being guided by and along the second end region of said anchor;

a fastener including an enlarged head portion and an externally threaded shank portion wherein, in an operative position, the shank portion of said fastener extends into threaded engagement with said anchor while the head portion of said fastener operably engages with said guide such that rotation of said fastener draws the first and second bone portions into relationship relative to each other.

11. The surgical fastener assembly according to claim 10 wherein said anchor is formed from a material chosen from the class comprised of: titanium, a titanium alloy, stainless steel, or a cobalt chromium alloy.

12. The surgical fastener assembly according to claim 10 wherein each pin in said series of pins is formed from a material chosen from the class comprised of: titanium, a titanium alloy, stainless steel, or a cobalt chromium alloy.

13. The surgical fastener assembly according to claim 10 wherein each pin in said series of pins is carried by said anchor for endwise displacement between said extended and retracted positions.

14. The surgical fastener assembly according to claim 10 wherein the second end of said anchor is configured to releasably accommodate a driving tool capable of imparting turning movements to said anchor.

15. The surgical fastener assembly according to claim 10 wherein said mechanism comprises a manually operated driver for effecting positive displacement of said pins in each direction between extended and retracted positions.

16. The surgical fastener assembly according to claim 10 further comprising a retainer carried toward and by the second end of said anchor and positionable relative to said fastener for releasably locking said fastener against inadvertent rotation thereby preventing axial displacement of the guide in a direction away from said anchor.

17. The surgical fastener assembly according to claim 10 wherein each pin in said series of pins has an arcuate configuration between opposite ends thereof.

18. The surgical fastener assembly according to claim 10 wherein said pins are equally disposed about an elongated axis of said anchor.

19. The surgical fastener assembly according to claim 10 wherein said anchor and said guide are configured with cooperating instrumentalities for preventing rotation relative to each other.

20. A surgical fastener assembly for coupling first and second bone portions across a fracture therebetween, said fastener assembly comprising:

an elongated anchor endwise insertable within the first bone portion such that a first end region of said anchor is disposed on one side of the fracture while a second end region of the anchor is disposed on an opposite side of the fracture;

a series of pins operably associated with said first end of said anchor for movement between extended and retracted positions, wherein when said pins are in said retracted position they have no operable anchoring effect between said anchor and the first bone portion, and wherein when said pins are in said extended position they radially extend outwardly from said anchor while remaining in operable association therewith thereby securing said anchor within the first bone portion;

a mechanism for positively moving said pins in opposite directions between said extended and retracted positions, wherein said mechanism comprises a driver mounted for free rotation within a cavity defined toward the first end of said anchor, said driver having external threading for engaging serrations on each of said pins whereby each pin is endwise and positively displaced in either direction of travel upon as a function of turning movements being imported to said driver;

a guide adapted to be fixedly secured to the second bone portion, with a projection on said guide being guided by and along the second end region of said anchor;

a fastener including an enlarged head portion and an externally threaded shank portion wherein, in an operative position, the shank portion of said fastener extends into threaded engagement with said anchor while the head portion of said fastener operably engages with said guide such that rotation of said fastener draws the first and second bone portions into relationship relative to each other.

21. The surgical fastener assembly according to claim 20 wherein said driver is configured at a trailing end thereof to releasably accommodate a tool adapted to impart turning movements to said driver.

22. The surgical fastener assembly according to claim 21 wherein said fastener is configured with an elongated axial bore for allowing said tool to pass endwise therethrough into operable engagement with said driver.

23. The surgical fastener assembly according to claim 22 further comprising a retainer carried toward and by the second end of said anchor and positionable relative to said fastener for releasably locking said fastener against inadvertent rotation thereby preventing axial displacement of the guide in a direction away from said anchor, said retainer defining an axial bore allowing endwise passage of said tool endwise therethrough.

24. A surgical fastener assembly for coupling first and second bone portions across a fracture therebetween, said fastener assembly comprising:

an elongated anchor endwise insertable within the first bone portion such that a first end region of said anchor is disposed on one side of the fracture while a second end region of the anchor is disposed on an opposite side of the fracture and wherein said anchor defines a series of axially elongated channels each channel having a blind forward end and an opposite end opening to the periphery of said anchor;

a series of pins, said pins accommodated within said series of axially elongated channels for endwise sliding movement therewithin and wherein said pins are operably associated with said first end of said anchor for movement between extended and retracted positions, wherein when said pins are in said retracted position they have no operable anchoring effect between said anchor and the first bone portion, and wherein when said pins are in said extended position they radially extend outwardly from said anchor while remaining in operable association therewith thereby securing said anchor within the first bone portion;

a mechanism for positively moving said pins in opposite directions between said extended and retracted positions;

a guide adapted to be fixedly secured to the second bone portion, with a projection on said guide being guided by and along the second end region of said anchor;

a fastener including an enlarged head portion and an externally threaded shank portion wherein, in an operative position, the shank portion of said fastener extends into threaded engagement with said anchor while the head portion of said fastener operably engages with said guide such that rotation of said fastener draws the first and second bone portions into relationship relative to each other.

25. The surgical fastener according to claim 24 wherein said channels are located in equally spaced relation relative to each other and about an elongated axis of said anchor.

26. The surgical fastener assembly according to claim 24 wherein each channel has a curvilinear configuration between opposite ends thereof.

27. A surgical fastener assembly for coupling first and second bone portions across a fracture therebetween said fastener assembly comprising:

an axially elongated bone screw defining an elongated axis and having external threading for anchoring a leading end of said bone screw endwise within the first bone portion such that the leading end portion of said anchor is disposed on one side of the fracture while a trailing end portion of the bone screw is disposed on an opposite side of the fracture, said bone screw defining an elongated bore and a series of axially elongated openings disposed about said axis, each opening being configured to intersect with said bore between opposite ends thereof and one end opening to the exterior of the bone screw;

a series of elongated pins configured for endwise reception and movement within said series of openings defined by said bone screw such that a lengthwise portion of each pin passes proximate to the elongated axis of said screw and moves between a retracted position, wherein said pins offer no operable anchoring effect for said bone screw, and an extended position, wherein said pins radially extend outwardly from said screw to significantly enhance anchorage of said screw within the bone;

a manually operated mechanism for effecting positive displacement of said pins in opposite direction relative to each other;

a guide adapted to be fixedly secured to the second bone portion, with a projection on said guide being guided by and along the second end portion of said bone screw; and a fastener including an enlarged head portion and an externally threaded shank portion, wherein the shank portion of said fastener extends into threaded engagement with the trailing end portion of said bone screw while the head portion of said fastener operably engages with said guide such that rotation of said fastener draws the first and second bone portions into relationship relative to each other.

28. The surgical fastener assembly according to claim 27 wherein said bone screw is formed from a material chosen from the class comprised of: titanium, a titanium alloy, stainless steel, or a cobalt chromium alloy.

29. The surgical fastener assembly according to claim 27 wherein each pin in said series of pins is formed from a material chosen from the class comprised of: titanium, a titanium alloy, stainless steel, or a cobalt chromium alloy.

30. The surgical fastener assembly according to claim 27 wherein the trailing end portion of said bone screw is configured to releasably accommodate a driving tool capable of imparting turning movements to said bone screw.

31. The surgical fastener assembly according to claim 27 wherein said mechanism comprises a manually operated driver for effecting positive displacement of said pins in each direction between extended and retracted positions.

32. The surgical fastener assembly according to claim 27 wherein said mechanism comprises a driver mounted for free rotation within said elongated bore toward the leading end portion of said bone screw, said driver having external threading for engaging serrations on each of said pins whereby each pin is endwise and positively displaced in either direction of travel upon as a function of turning movements being imparted to said driver.

33. The surgical fastener assembly according to claim 32 wherein said driver is configured at a trailing end thereof to releasably accommodate a tool adapted to impart turning movements to said driver.

34. The surgical fastener assembly according to claim 33 wherein said fastener is configured with an elongated axial bore for allowing said tool to pass endwise therethrough into operable engagement with said driver.

35. The surgical fastener assembly according to claim 33 further comprising a retainer carried toward and by the trailing end portion of said bone screw and positionable relative to said fastener for releasably locking said fastener against inadvertent rotation thereby preventing axial displacement of the guide in a direction away from said bone screw, said retainer defining an axial bore allowing endwise passage of said tool endwise therethrough.

36. The surgical fastener assembly according to claim 27 further comprising a retainer carried toward and by the trailing end portion of said bone screw and positionable relative to said fastener for releasably locking said fastener against inadvertent rotation thereby preventing axial displacement of the guide in a direction away from said bone screw.

37. The surgical fastener assembly according to claim 27 wherein each pin in said series of pins has an arcuate configuration between opposite ends thereof.

38. The surgical fastener assembly according to claim 27 wherein said pins are equally disposed about and relative to an elongated axis of said bone screw.

39. The surgical fastener assembly according to claim 27 wherein said bone screw defines a series of axially elongated channels for accommodating the pins for endwise sliding movement therewithin, each channel having a blind forward end and an opposite end opening to the periphery of said bone screw.

40. The surgical fastener assembly according to claim 39 wherein said channels are located in equally spaced relation relative to each other and about an elongated axis of said bone screw.

41. The surgical fastener assembly according to claim 39 wherein each channel has a curvilinear configuration between opposite ends thereof.

42. The surgical fastener assembly according to claim 27 wherein said bone screw and said guide are configured with cooperating instrumentalities for preventing rotation relative to each other.

43. A hip pinning system for compressively interconnecting first and second fractured bones segments, said hip pinning system comprising:
an axially elongated bone screw defining an elongated axis and having external threading extending axially therealong for anchoring a leading end portion of said bone screw endwise within the first bone segment such that the leading end portion of said bone screw is disposed on one side of the fracture while a trailing end portion of said bone screw is disposed on an opposite side of the fracture, said bone screw defining an elongated axial bore and a series of elongated arcuate openings intersecting with said bore between opposite ends thereof and having one end opening to an exterior of said bone screw;
a series of elongated and arcuate shaped pins configured for endwise reception within said series of arcuate openings defined by said bone screw such that a lengthwise portion of each pin passes through said bore and is movable between a retracted position, wherein said pins offer substantially no anchoring effect, and an extended position, wherein said pins radially extend from said bone screw to significantly enhance securement of said bone screw within said bone;
a driver arranged for turning movement in said bore of the bone screw and which is operably associated with each pin whereby turning movements of said driver positively effects endwise and substantially concomitant displacement of said pins in opposite directions within their respective openings and radially relative to said bone screw as a function of the direction of rotation of said driver;
a guide adapted to be fixedly secured to the second bone segment, with a projection on said guide being guided by and along the trailing end portion of said bone screw; and
a fastener including an enlarged head portion and an externally threaded shank portion, wherein the shank portion of said fastener extends into threaded engagement with the trailing end portion of said bone screw while the head portion of said fastener operably engages with said guide such that rotation of said fastener draws the first and second bone segments into compressive relationship relative to each other.

44. The hip pinning system according to claim 43 wherein said bone screw is configured toward the trailing end portion thereof to releasably accommodate a driving tool.

45. The hip pinning system according to claim 43 wherein the leading end portion of said bone screw is generally pointed to facilitate insertion and self-tapping of the bone screw into the substance of the first bone segment.

46. The hip pinning system according to claim 43 wherein the bore defined by said bone screw is configured with a blind cavity portion extending axially along said axis toward the leading end portion of said bone screw and an internally threaded portion arranged in axially adjacent relation relative to each other, said internally threaded portion opening to the trailing end of said bone screw.

47. The hip pinning system according to claim 46 wherein said driver is arranged for free turning movements within the blind cavity portion of the bore defined by said bone screw.

48. The hip pinning system according to claim 43 wherein said driver includes an axially elongated externally threaded member having leading and trailing ends.

49. The hip pinning system according to claim 48 wherein the trailing end portion of said axially elongated member is configured to releasably accommodate a driving tool capable of imparting turning movements to said driver.

50. The hip pinning system according to claim 49 wherein said fastener is configured with an elongated axial bore for allowing said tool to pass endwise therethrough into operable engagement with said driver.

51. The hip pinning system according to claim 50 further comprising a retainer carried toward and by the trailing end portion of said bone screw and positionable relative to said fastener for releasably locking said fastener against inadvertent rotation thereby preventing axial displacement of the guide in a direction away from said bone screw, said retainer defining an axial bore allowing endwise passage of said tool endwise therethrough.

52. The hip pinning system according to claim 43 further comprising a retainer carried toward and by the trailing end portion of said bone screw and positionable relative to said fastener for releasably locking said fastener against inadvertent rotation thereby preventing axial displacement of the guide in a direction away from said bone screw.

53. A surgical fastener for coupling first and second bone portions together across a fracture, comprising:

an anchor member, said anchor member including external threading extending along a first portion thereof and having a bore extending substantially axially therethrough between first and second ends of the anchor member wherein, when in an operative position, the first portion of the anchor member including the first end thereof is mounted in the first bone portion and a second portion of the anchor member extends away from the first bone portion into the second bone portion;

a guide adapted to be fixedly coupled to the second bone portion, wherein the guide includes a sleeve which, in the operative position, is received around the second portion of the anchor member;

a compression screw which, in the operative position, engages an abutting surface of the guide and extends into the bore to threadably engage the anchor member so that rotation of the compression screw in a first direction draws the guide toward the anchor member while rotation of the compression screw in a second direction opposite to the first direction allows movement of the guide member with respect to the anchor member;

a pin movably received within the anchor member for movement between an insertion/retraction position in which the pin is received within the anchor member and an extended position in which at least a tissue anchoring end of the pin extends from an outer surface of the anchor member; and a pin retraction/extension mechanism extending from the anchor member to the guide for moving, in an extension mode, the tissue anchoring end of the pin away from the insertion/retraction position and, in a retraction mode for drawing the tissue anchoring end of the pin toward the insertion/retraction position.

\* \* \* \* \*